United States Patent [19]

Lang

[11] Patent Number: 4,656,165
[45] Date of Patent: Apr. 7, 1987

[54] AMINOMETHYL PENEM COMPOUNDS

[75] Inventor: Marc Lang, Rixheim, France

[73] Assignee: Ciba-Geigy Corporation, Ardsley, N.Y.

[21] Appl. No.: 644,887

[22] Filed: Aug. 27, 1984

[30] Foreign Application Priority Data

Sep. 2, 1983 [CH] Switzerland .................. 4831/83
May 22, 1984 [CH] Switzerland .................. 2510/84

[51] Int. Cl.⁴ .................. C07D 499/00; A61K 31/425
[52] U.S. Cl. ................................ 514/192; 540/310
[58] Field of Search .................. 260/245.2 R, 245.2 T; 514/192

[56] References Cited

U.S. PATENT DOCUMENTS

| 4,272,437 | 6/1981 | Menard et al. | 424/246 |
| 4,347,183 | 8/1983 | Afonso et al. | 424/246 |
| 4,386,030 | 5/1983 | Christensen et al. | 424/246 |

FOREIGN PATENT DOCUMENTS

| 0003960 | 9/1979 | European Pat. Off. |
| 0069373 | 1/1983 | European Pat. Off. |
| 0070204 | 1/1983 | European Pat. Off. |
| 0109044 | 5/1984 | European Pat. Off. |
| 56-166194 | 12/1981 | Japan |
| 2043639 | 10/1980 | United Kingdom |

Primary Examiner—Nicholas S. Rizzo
Attorney, Agent, or Firm—Michael W. Glynn; Irving M. Fishman

[57] ABSTRACT

Compounds of the formula

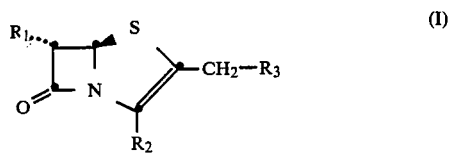

in which
$R_1$ is lower alkyl substituted by hydroxy or by protected hydroxy,
$R_2$ represents carboxy or functionally modified carboxy, and
$R_3$ represents amino, lower alkyl-substituted amino, substituted methyleneamino or protected amino, optical isomers of compounds of the formula I, mixtures of these optical isomers, and salts of such compounds of the formula I that have a salt-forming group have antibiotic activity. The compounds of the formula I are manufactured according to processes that are known per se.

5 Claims, No Drawings

AMINOMETHYL PENEM COMPOUNDS

The present invention relates to novel 2-aminomethylpenem compounds, to processes for their manufacture, to pharmaceutical preparations that contain such compounds, and to their use for the manufacture of pharmaceutical preparations or as pharmacologically active compounds.

The invention relates especially to substantially optically pure 2-aminomethyl-2-penem compounds of the formula

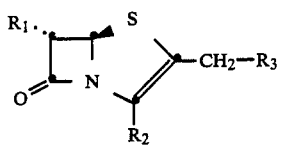

(I)

in which $R_1$ is lower alkyl substituted by hydroxy or by protected hydroxy, $R_2$ represents carboxy or functionally modified carboxy, and $R_3$ represents amino, lower alkyl-substituted amino, substituted methyleneamino or protected amino, optical isomers of compounds of the formula I that have a chirality centre in the radical $R_1$, mixtures of these optical isomers, and salts of such compounds of the formula I having a salt-forming group.

Within the scope of the present description, the definitions used hereinbefore and hereinafter have preferably the following meanings:

Functionally modified carboxy $R_2$ is especially esterified carboxy that can be cleaved under physiological conditions or protected carboxy $R_2'$.

An esterified carboxy group $R_2$ that can be cleaved under physiological conditions protects the compounds of the formula I from salt formation in the gastro-intestinal tract in the case of oral administration thus preventing premature excretion, and is especially an acyloxymethoxycarbonyl group in which acyl represents, for example, the radical of an organic carboxylic acid, especially an optionally substituted lower alkanecarboxylic acid, or in which acyloxymethyl forms the radical of a lactone. Such groups are, for example, lower alkanoyloxymethoxycarbonyl, amino-lower alkanoyloxymethoxycarbonyl, especially α-amino-lower alkanoyloxymethoxycarbonyl, 4-crotonolactonyl and 4-butyrolacton-4-yl. Further esterified carboxy groups $R_2$ that can be cleaved under physiological conditions are, for example, 5-indanyloxycarbonyl, 3-phthalidyloxycarbonyl, 1-lower alkoxycarbonyloxy-lower alkoxycarbonyl, 1-lower alkoxy-lower alkoxycarbonyl or 2-oxo-1,3-dioxolen-4-ylmethoxycarbonyl which is optionally substituted by lower alkyl or phenyl in the 5-position of the dioxolene ring.

Lower alkyl-substituted amino $R_3$ is, for example, lower alkylamino or di-lower alkylamino.

In substituted methyleneamino $R_3$, the methylene radical is preferably mono- or di-substituted. Substituted methyleneamino is, for example, a group of the formula

(IA)

in which $X_1$ represents hydrogen, optionally substituted amino, for example amino, lower alkylamino, di-lower alkylamino, lower alkyleneamino, nitroamino, hydrazino or anilino, etherified hydroxy, for example lower alkoxy or phenyl-lower alkoxy, etherified mercapto, for example lower alkylthio, optionally substituted lower alkyl, for example lower alkyl, amino-lower alkyl, N-lower alkylamino-lower alkyl or N,N-di-lower alkylamino-lower alkyl, lower alkenyl, phenyl or monocyclic heteroaryl, such as corresponding 5- or 6-membered heteroaryl having 1 or 2 nitrogen atoms and/or an oxygen or sulphur atom, such as pyridyl, for example 2- or 4-pyridyl, thienyl, for example 2-thienyl, or thiazolyl, for example 4-thiazolyl, and $X_2$ represents optionally substituted amino, for example amino, lower alkylamino, di-lower alkylamino, lower alkyleneamino, cyanamino, hydrazino or anilino, etherified hydroxy, for example lower alkoxy or phenyl-lower alkoxy, or etherified mercapto, for example lower alkylthio.

In preferred radicals of the formula (IA), $X_1$ represents hydrogen, amino, lower alkylamino or lower alkyl and $X_2$ represents amino.

Radicals of the formula (IA) that have a hydrogen atom at the α-atom of the substituent $X_1$ and/or the substituent $X_2$, for example radicals of the formula (IA) in which $X_1$ represents amino, lower alkylamino, nitroamino, hydrazino, anilino or optionally substituted lower alkyl and/or $X_2$ represents amino, lower alkylamino, hydrazino or anilino, can also be in one of the tautomeric forms

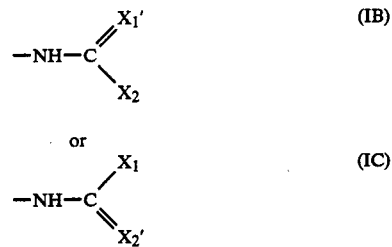

in which $X_1'$ and $X_2'$ each represents corresponding substituted or unsubstituted methylene or imino.

In the present description, the term "lower" used in connection with definitions of groups and compounds denotes that, unless expressly defined otherwise, the groups and compounds so designated contain up to 7, preferably up to 4, carbon atoms.

Hydroxy-substituted lower alkyl $R_1$ is especially lower alkyl substituted by hydroxy in the α-position relative to the penem ring structure and represents, for example, 1-hydroxyprop-1-yl, 2-hydroxybut-2-yl or, especially, hydroxymethyl or 1-hydroxyethyl.

Lower alkanoyloxymethoxycarbonyl is, for example, acetoxymethoxycarbonyl or pivaloyloxymethoxycarbonyl.

α-amino-lower alkanoyloxymethoxycarbonyl is, for example, glycyloxymethoxycarbonyl, L-valyloxymethoxycarbonyl or L-leucyloxymethoxycarbonyl.

1-lower alkoxycarbonyloxy-lower alkoxycarbonyl is, for example, ethoxycarbonyloxymethoxycarbonyl or 1-ethoxycarbonyloxyethoxycarbonyl.

1-lower alkoxy-lower alkoxycarbonyl is, for example, methoxymethoxycarbonyl or 1-methoxyethoxycarbonyl.

A 2-oxo-1,3-dioxolen-4-ylmethoxy group which is optionally substituted by lower alkyl or phenyl in the 5-position of the dioxolene ring is especially a 5-phenyl-2-oxo-1,3-dioxolen-4-ylmethoxy group and, more especially, a 5-methyl-2-oxo-1,3-dioxolen-4-ylmethoxy group.

Lower alkylamino is, for example, methylamino, ethylamino, n-propylamino, isopropylamino or n-butylamino, whilst di-lower alkylamino represents, for example, dimethylamino, diethylamino, di-n-propylamino or di-n-butylamino.

Lower alkyleneamino has especially from 4 to 6 carbon chain members and represents, for example, pyrrolidino or piperidino.

Lower alkoxy is, for example, methoxy, ethoxy, n-propoxy, isopropoxy, n-butoxy or tert.-butoxy, whilst phenyl-lower alkoxy is, for example, benzyloxy.

Lower alkylthio is, for example, methylthio, ethylthio, n-propylthio, isopropylthio or n-butylthio.

Lower alkyl is, for example, methyl, ethyl, n-propyl, isopropyl, n-butyl, isobutyl, sec.-butyl or tert.-butyl.

Amino-lower alkyl is, for example, 2-aminoethyl or 3-aminopropyl.

N-lower alkylamino-lower alkyl is, for example, 2-methyl- or 2-ethyl-aminoethyl, whilst N,N-di-lower alkylamino-lower alkyl represents, for example, 2-dimethylaminoethyl or 2-diethylaminoethyl.

Lower alkenyl is, for example, allyl, n-propenyl or isopropenyl.

Preferred esterified carboxy groups $R_2$ that can be cleaved under physiological conditions are, for example, phthalidyloxycarbonyl, lower alkanoyloxymethoxycarbonyl, for example acetoxymethoxycarbonyl or pivaloyloxymethoxycarbonyl, and 1-lower alkoxycarbonyloxy-lower alkoxycarbonyl, for example 1-ethoxycarbonyloxyethoxycarbonyl.

A preferred embodiment of the present invention relates to compounds of the formula I in which $R_1$ is hydroxymethyl and $R_2$ and $R_3$ have the meanings given under formula I.

A further preferred embodiment of the present invention relates to compounds of the formula I in which $R_1$ is 1-hydroxyethyl and $R_2$ and $R_3$ have the meanings given under formula I.

The functional groups present in compounds of the formula I, such as hydroxy, carboxy or amino groups, especially the hydroxy group in the radical $R_1$ and the carboxy group $R_2$ are optionally protected by protecting groups used in penem, penicillin, cephalosporin and peptide chemistry. Such protecting groups protect the functional groups in question from undesired condensation reactions, substitution reactions and the like during the synthesis of the compound of the formula I from its precursors.

Such protecting groups can be removed readily, that is to say without undesirable secondary reactions taking place, for example by means of solvolysis or reduction, or alternatively under physiological conditions.

Protecting groups of this type and the methods by which they are introduced and removed are described, for example, in J. F. W. McOmie, "Protective Groups in Organic Chemistry", Plenum Press, London, New York, 1973, T. W. Greene, "Protective Groups in Organic Synthesis", Wiley, New York, 1981, "The Peptides", Vol. I, Schroeder and Luebke, Academic Press, London, New York, 1965 and Houben-Weyl, "Methoden der Organischen Chemie", Volume 15/1, Georg Thieme Verlag, Stuttgart, 1974.

In compounds of the formula (I), a hydroxy group in the radical $R_1$ may be protected, for example, by acyl radicals. Suitable acyl radicals are, for example, lower alkanoyl optionally substituted by halogen, for example acetyl or trifluoroacetyl, benzoyl optionally substituted by nitro, for example benzoyl, 4-nitrobenzoyl or 2,4-dinitrobenzoyl, lower alkoxycarbonyl optionally substituted by halogen, for example 2-bromoethoxycarbonyl or 2,2,2-trichloroethoxycarbonyl, lower alkenyloxycarbonyl, for example allyloxycarbonyl, or phenyl-lower alkoxycarbonyl optionally substituted by nitro, for example 4-nitrobenzyloxycarbonyl. Further suitable hydroxy-protecting groups are, for example, tri-substituted silyl, such as tri-lower alkylsilyl, for example trimethylsilyl or tert.-butyldimethylsilyl, 2-halo-lower alkyl groups, for example 2-chloro-, 2-bromo-, 2-iodo- and 2,2,2-trichloro-ethyl, and phenyl-lower alkyl optionally substituted by halogen, for example chlorine, lower alkoxy, for example methoxy, and/or by nitro, such as corresponding benzyl. Tri-lower alkylsilyl, lower alkenyloxycarbonyl and halo-substituted lower alkoxycarbonyl are preferred as hydroxy-protecting groups.

A carboxy group $R_2$ is customarily protected in esterified form, the ester group being readily cleavable under mild conditions, for example under mildly reductive, such as hydrogenolytic, conditions, or under mildly solvolytic, such as acidolytic or especially basic or neutral hydrolytic, conditions. A protected carboxy group can also be an esterified carboxy group that can readily be converted into a different functionally modified carboxy group, such as into a different esterified carboxy group.

Such esterified carboxy groups contain as esterifying groups especially lower alkyl groups that are branched in the 1-position or suitably substituted in the 1- or 2-position. Preferred carboxy groups in esterified form are, inter alia, lower alkoxycarbonyl, for example methoxycarbonyl, ethoxycarbonyl, isopropoxycarbonyl or tert.-butoxycarbonyl, and (hetero)arylmethoxycarbonyl having from 1 to 3 aryl radicals or having a monocyclic heteroaryl radical, these optionally being mono- or poly-substituted, for example by lower alkyl, such as tert.-lower alkyl, for example tert.-butyl, halogen, for example chlorine, and/or by nitro. Examples of such groups are benzyloxycarbonyl optionally substituted, for example, as mentioned above, for example 4-nitrobenzyloxycarbonyl, diphenylmethoxycarbonyl or triphenylmethoxycarbonyl optionally substituted, for example, as mentioned above, for example diphenylmethoxycarbonyl, or picolyloxycarbonyl, for example 4-picolyloxycarbonyl, or furfuryloxycarbonyl, such as 2-furfuryloxycarbonyl, each optionally substituted, for example, as mentioned above. Further suitable groups are lower alkanoylmethoxycarbonyl, such as acetonyloxycarbonyl, aroylmethoxycarbonyl, in which the aroyl group preferably represents benzoyl optionally substituted, for example, by halogen, such as bromine, for example phenacyloxycarbonyl, halo-lower alkoxycarbonyl, such as 2-halo-lower alkoxycarbonyl, for example 2,2,2-trichloroethoxycarbonyl, 2-chloroethoxycarbonyl, 2-bromoethoxycarbonyl or 2-iodoethoxycarbonyl, or ω-halo-lower alkoxycarbonyl in which lower alkoxy contains from 4 to 7 carbon atoms, for example 4-chlorobutoxycarbonyl, phthalimidomethoxycarbonyl, lower alkenyloxycarbonyl, for example allyloxycarbonyl, or ethoxycarbonyl substituted in the 2-position by lower alkylsulphonyl, cyano or by tri-substituted silyl, such as tri-lower alkylsilyl or triphenylsilyl, for example 2-methylsulphonylethoxycarbonyl, 2-cyanoethoxycarbonyl, 2-trimethylsilylethoxycarbonyl or 2-(di-n-butylmethylsilyl)-ethoxycarbonyl.

Other protected carboxy groups in esterified form are corresponding organic silyloxycarbonyl groups, and also corresponding organic stannyloxycarbonyl groups. In these groups the silicon or tin atom preferably has lower alkyl, especially methyl or ethyl, and also lower alkoxy, for example methoxy, as substituents. Suitable silyl and stannyl groups are especially tri-lower alkylsilyl, especially trimethylsilyl or dimethyl-tert.-butylsilyl, or correspondingly substituted stannyl groups, for example tri-n-butylstannyl.

Preferred protected carboxy groups $R_2'$ are the 4-nitrobenzyloxycarbonyl and lower alkenyloxycarbonyl, especially allyloxycarbonyl, groups and the ethoxycarbonyl group substituted in the 2-position by lower alkylsulphonyl, cyano or by tri-lower alkylsilyl, for example trimethylsilyl or di-n-butylmethylsilyl.

A protected amino group in the radical $R_3$ can be, for example, in the form of a readily cleavable acylamino, acylimino, etherified mercaptoamino, silylamino or stannylamino group or in the form of an enamino, nitro or azido group.

In a corresponding acylamino group, acyl is, for example, the acyl radical of an organic acid having, for example, up to 18 carbon atoms, especially an alkanecarboxylic acid optionally substituted, for example, by halogen or phenyl, or of a benzoic acid optionally substituted, for example, by halogen, lower alkoxy or nitro, or of a carbonic acid semiester. Such acyl groups are, for example, lower alkanoyl, such as formyl, acetyl or propionyl, halo-lower alkanoyl, such as 2-haloacetyl, especially 2-fluoro-, 2-bromo-, 2-iodo-, 2,2,2-trifluoro- or 2,2,2-trichloro-acetyl, optionally substituted benzoyl, for example benzoyl, halobenzoyl, such as 4-chlorobenzoyl, lower alkoxybenzoyl, such as 4-methoxybenzoyl, or nitrobenzoyl, such as 4-nitrobenzoyl. Especially suitable are also lower alkenyloxycarbonyl, for example allyloxycarbonyl, or lower alkoxycarbonyl optionally substituted in the 1- or 2-position, such as lower alkoxycarbonyl, for example methoxy- or ethoxy-carbonyl, optionally substituted benzyloxycarbonyl, for example benzyloxycarbonyl or 4-nitrobenzyloxycarbonyl, aroylmethoxycarbonyl in which the aroyl group preferably represents benzoyl optionally substituted, for example, by halogen, such as bromine, for example phenacyloxycarbonyl, 2-halo-lower alkoxycarbonyl, for example 2,2,2-trichloroethoxycarbonyl, 2-chloroethoxycarbonyl, 2-bromoethoxycarbonyl or 2-iodoethoxycarbonyl, or 2-(tri-substituted silyl)-ethoxycarbonyl, such as 2-tri-lower alkylsilylethoxycarbonyl, for example 2trimethylsilylethoxycarbonyl or 2-(di-n-butylmethylsilyl)-ethoxycarbonyl, or 2-triarylsilylethoxycarbonyl, such as 2-triphenylsilylethoxycarbonyl.

In an acylimino group, acyl is, for example, the acyl radical of an organic dicarboxylic acid having, for example, up to 12 carbon atoms, especially of a corresponding aromatic dicarboxylic acid, such as phthalic acid. Such a group is especially phthalimino.

An etherified mercaptoamino group is especially a phenylthioamino group optionally substituted by lower alkyl, such as methyl or tert.-butyl, lower alkoxy, such as methoxy, halogen, such as chlorine or bromine, and/or by nitro, or a pyridylthioamino group. Corresponding groups are, for example, 2- or 4-nitrophenylthioamino or 2-pyridylthioamino.

A silyl- or stannyl-amino group is especially an organic silyl- or stannyl-amino group in which the silicon or tin atom preferably contains as substituent(s) lower alkyl, for example methyl, ethyl, n-butyl or tert.-butyl, also lower alkoxy, for example methoxy. Corresponding silyl or stannyl groups are especially tri-lower alkylsilyl, especially trimethylsilyl, also dimethyl-tert.-butylsilyl, or correspondingly substituted stannyl, for example tri-n-butylstannyl.

Further protected amino groups are, for example, enamino groups that contain an electron-attracting substituent, for example a carbonyl group, at the double bond in the 2-position. Protecting groups of this type are, for example, 1-acyl-lower alk-1-en-2-yl radicals in which acyl represents, for example, the corresponding radical of a lower alkanecarboxylic acid, for example acetic acid, of a benzoic acid optionally substituted, for example, by lower alkyl, such as methyl or tert.-butyl, lower alkoxy, such as methoxy, halogen, such as chlorine, and/or by nitro, or especially of a carbonic acid semiester, such as a carbonic acid lower alkyl semiester, for example a carbonic acid methyl semiester or ethyl semiester, and in which lower alk-1-ene represents especially 1-propene. Corresponding protecting groups are especially 1-lower alkanoylprop-1-en-2-yl, for example 1-acetylprop-1-en-2-yl, or 1-lower alkoxycarbonylprop-1-en-2-yl, for example 1-ethoxycarbonylprop-1-en-2-yl.

Preferred protected amino groups are, for example, azido, phthalimido, nitro, lower alkenyloxycarbonylamino, optionally nitro-substituted benzyloxycarbonylamino, 1-lower alkanoyl-lower alk-1-en-2-ylamino or 1-lower alkoxycarbonyl-lower alk-1-en-2-ylamino.

Salts of compounds according to the invention are especially pharmaceutically acceptable, non-toxic salts of compounds of the formula I. Such salts are formed, for example, from acidic groups, for example the carboxy groups $R_2$, present in compounds of the formula I and are especially metal or ammonium salts, such as alkali metal and alkaline earth metal salts, for example sodium, potassium, magnesium or calcium salts, and ammonium salts with ammonia or suitable organic amines, such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, dibenzylamine or N-benzyl-β-phenethylamine. Compounds of the formula I having a basic group, for example having an amino group, can form acid addition salts, for example with inorganic acids, such as hydrochloric acid, sulphuric acid or phosphoric acid, or with suitable organic carboxylic or sulphonic acids, for example acetic acid, succinic acid, fumaric acid, maleic acid, tartaric acid, oxalic acid, citric acid, benzoic acid, mandelic acid, malic acid, ascorbic acid, methanesulphonic acid or 4-toluenesulphonic acid. Compounds of the formula I having an acidic group and a basic group can also be in the form of internal salts, that is to say in zwitterionic form.

For the purposes of isolation or purification it is also possible to use pharmaceutically unacceptable salts. Only the pharmaceutically acceptable, non-toxic salts are used therapeutically and these are therefore preferred.

The penem compounds of the formula I have the R-configuration at the 5-carbon atom and the S-configuration at the 6-carbon atom. The compounds of the formula I can have in the substituent $R_1$ a further chirality centre which can be in the R-, S- or the racemic R,S-configuration. In preferred compounds of the formula I, a radical $R_1$ which is asymmetrically substituted in the α-position (at the 1'-carbon atom) by hydroxy, especially 1'-hydroxyethyl, has the R-configuration.

The compounds of the formula I are in substantially optically pure form, that is to say they are substantially free of isomers having a configuration other than the (5R,6S)-configuration and, especially, free of the corresponding (5S,6R)-isomers.

In a preferred group of compounds of the formula I $R_1$ is lower alkyl substituted by hydroxy or by protected hydroxy, $R_2$ is carboxy or functionally modified carboxy and $R_3$ is amino or protected amino.

In a further preferred group of compounds of the formula I $R_1$ is lower alkyl substituted by hydroxy or by protected hydroxy, $R_2$ is carboxy or functionally modified carboxy and $R_3$ is amino substituted by lower alkyl, or substituted methyleneamino.

The invention relates especially to compounds of the formula I in which $R_1$ is lower alkyl substituted by hydroxy or by protected hydroxy, $R_2$ represents carboxy, esterified carboxy that can be cleaved under physiological conditions, or protected carboxy $R_2'$, and $R_3$ represents amino, lower alkylamino, di-lower alkylamino, a group of the formula $-N=C(X_1,X_2)$ in which $X_1$ is hydrogen, amino, lower alkylamino, di-lower alkylamino, lower alkyleneamino, nitroamino, hydrazino, anilino, lower alkoxy, phenyl-lower alkoxy, lower alkylthio, lower alkyl, amino-lower alkyl, N-lower alkylamino-lower alkyl, N,N-di-lower alkylamino-lower alkyl, lower alkenyl, phenyl, pyridyl, for example 2- or 4-pyridyl, thienyl, for example 2-thienyl, or thiazolyl, for example 4-thiazolyl, and $X_2$ is amino, lower alkylamino, di-lower alkylamino, lower alkyleneamino, cyanamino, hydrazino, anilino, lower alkoxy, phenyl-lower alkoxy or lower alkylthio, or $R_3$ represents protected amino, to optical isomers of compounds of the formula I that have a chirality centre in the radical $R_1$, mixtures of these optical isomers, and salts of such compounds of the formula I that have a salt-forming group, in substantially optically pure form.

The invention relates more especially to compounds of the formula I in which $R_1$ is lower alkyl substituted in the α-position by hydroxy, tri-lower alkylsilyloxy, 2-halo-lower alkoxy, 2-halo-lower alkoxycarbonyloxy, lower alkenyloxycarbonyloxy or by optionally nitro-substituted phenyl-lower alkoxycarbonyloxy, $R_2$ represents carboxy, lower alkenyloxycarbonyl, optionally nitro-substituted benzyloxycarbonyl, lower alkanoylmethoxycarbonyl, 2-halo-lower alkoxycarbonyl, 2-tri-lower alkylsilylethoxycarbonyl or an esterified carboxy group that can be cleaved under physiological conditions, for example 1-lower alkoxycarbonyloxy-lower alkoxycarbonyl, lower alkanoyloxymethoxycarbonyl, α-amino-lower alkanoyloxymethoxycarbonyl or phthalidyloxycarbonyl, $R_3$ represents amino, lower alkylamino, di-lower alkylamino, a group of the formula $-N=C(X_1,X_2)$ in which $X_1$ is hydrogen, amino, lower alkylamino, lower alkyl, phenyl or pyridyl, for example 2-pyridyl, and $X_2$ is amino, lower alkylamino or di-lower alkylamino, or $R_3$ represents azido, phthalimino, nitro, lower alkenyloxycarbonylamino, optionally nitro-substituted benzyloxycarbonylamino, 1-lower alkanoyl-lower alk-1-en-2-ylamino or 1-lower alkoxycarbonyl-lower alk-1-en-2-ylamino, to optical isomers of compounds of the formula I that have a chirality centre in the radical $R_1$, mixtures of these optical isomers, and salts of such compounds of the formula I that have a salt-forming group, in substantially optically pure form.

The invention relates more especially to compounds of the formula I in which $R_1$ is lower alkyl substituted in the α-position by hydroxy, and $R_2$ represents carboxy or an esterified carboxy group that can be cleaved under physiological conditions, for example, 1-lower alkoxycarbonyloxy-lower alkoxycarbonyl or lower alkanoyloxymethoxycarbonyl, and $R_3$ represents amino, lower alkylamino or formamidino, to optical isomers of compounds of the formula I that have a chirality centre in the radical $R_1$, and mixtures of these optical isomers, and salts of such compounds of the formula I that have a salt-forming group, in substantially optically pure form.

The invention relates chiefly to compounds of the formula I in which R represents hydroxymethyl or 1-hydroxyethyl, $R_2$ is carboxy and $R_3$ represents amino, and to salts thereof, in substantially optically pure form.

The invention also relates above all to the pure optical isomers of those compounds of the formula I that have a chirality centre in the substituent $R_1$, especially the (1'R)-isomer of compounds of the formula I in which $R_1$ is 1'-hydroxyethyl, and to salts of such compounds of the formula I that have a salt-forming group.

The invention relates especially to the compounds of the formula I mentioned in the Examples and to the pharmaceutically acceptable salts thereof.

The compounds of the present invention can be manufactured by processes know per se.

The novel compounds are manufactured, for example, as follows:

(a) in a compound of the formula

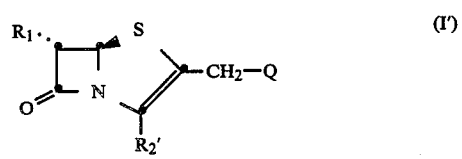

in which $R_1$ has the meaning given under formula (I), $R_2'$ is a protected carboxy group and Q is a group that can be converted into the radical $R_3$, the group Q is converted into the radical $R_3$, or (b) an ylide compound of the formula

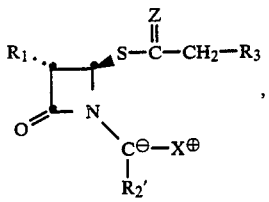

(II)

in which R₁ and R₃ have the meanings given under formula I, R₂' reperesents a protected carboxy group, Z represents oxygen or sulphur and X⊕ represents either a tri-substituted phosphonio group, or a di-esterified phosphono group together with a cation, is cyclised, or (c) a compound of the formula

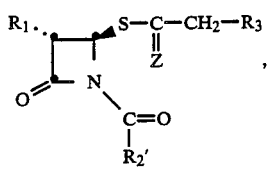

(III)

in which R₁ and R₃ have the meanings given under formula I, Z is oxygen or sulphur and R₂' is a protected carboxy group is treated with an orgainic compound of trivalent phosphorus, (d) in a compound of the formula

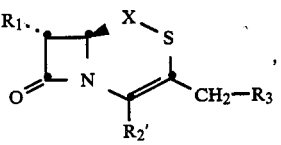

(III')

in which R₁ and R₃ have the meanings given under formula I, R₂' represents a protected carboxy group and X represents the group —S— or the group —SO₂—, the radical X is removed, and, if desired or necessary, in a resulting compound of the formula I, a protected hydroxy group in the radical R₁ is converted into a free hydroxy group, and/or, if desired, in a resulting compound of the formula I, a protected carboxy group R₂' is converted into a free carboxy group, into an esterified carboxy group that can be cleaved under physiological conditions or into a different protected carboxy group R₂', or a free carboxy group R₂ is converted into an esterified carboxy group that can be cleaved under physiological conditions or into a protected carboxy group R₂', and/or, if desired, a protected amino group R₃ is converted into a free amino group, or a free amino group R₃ is converted into a substituted amino group, and/or, if desired, a resulting compound having a salt-forming group is converted into a salt, or a resulting salt is converted into the free compound or into a different salt, and/or, if desired, a resulting mixture of isomeric compounds of the formula I is separated into the individual isomers.

In starting compounds of the formulae I', II and III, functional groups, such as a free hydroxy group in the radical R₁, and especially a free amino group R₃, are preferably protected by conventional protecting groups, for example by one of those mentioned above.

(a) Introduction of the radical R₃

A group Q that can be converted into a radical R₃ is especially a corresponding group that can be converted by nucleophilic reaction. Such groups Q are especially esterified hydroxy groups, such as hydroxy groups esterified by a hydrohalic acid, a di-lower alkyl- or diarylphosphoric acid, an optionally oxo- or halo-substituted lower alkanecarboxylic acid, an optionally halo-substituted lower alkanesulphonic acid, or by an optionally halo- or lower alkyl-substituted benzenesulphonic acid. Such groups Q are, for example, halogen, such as chlorine, bromine or iodine, di-lower alkyl- or diaryl-phosphoryloxy, for example dimethyl-, diethyl- or diphenylphosphoryloxy, optionally halo- or oxo-substituted lower alkanoyloxy, for example formyloxy, acetoxy or acetoacetoxy, optionally halo-substituted lower alkanesulphonyloxy, for example methanesulphonyloxy or trifluoromethanesulphonyloxy, or optionally halo- or lower alkyl-substituted benzenesulphonyloxy, for example benzenesulphonyloxy, 4-chloro-, 4-bromo- or 4-methyl-benzenesulphonyloxy.

The reaction is carried out with a compound of the formula R₃—H in which R₃ has the meanings given above, or with a salt, such as an alkali metal salt, for example the sodium or potassium salt, thereof, that is to say with hydrazoic acid or with phthalimide or, especially, with alkali metal salts, for example the sodium or potassium salt, thereof, and also with ammonia, lower alkyl- and di-lower alkyl-amines, amidines, guanidines and the like, each of which is optionally in protected form, it being necessary, however, for at least one hydrogen atom to be present at the reacting amino group. The reaction is carried out in an inert solvent, such as, for example, a lower alkanol, dimethylformamide, a cyclic ether, for example dioxan, or in dimethyl sulphoxide, at room temperature or at slightly elevated or reduced temperature, for example at approximately from 0° to 40° C., especially at room temperature.

The starting compounds of the formula (I') can be manufactured in a manner analogous to that described under process (b) by cyclisation of the phosphorane of the formula

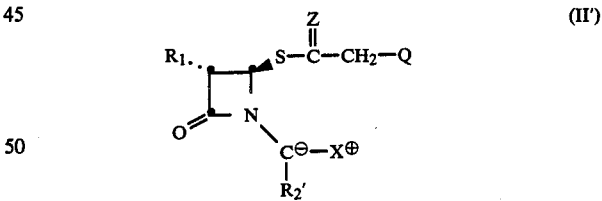

(II')

in which Z and X⊕ have the meanings given under formula (II).

(b) Cyclisation of the compound of the formula II

The group X⊕ in a starting material of the formula II is one of the phosphonio or phosphono groups customarily used in Wittig condensation reactions, especially a triaryl-, for example triphenyl-, or tri-lower alkyl-, for example tri-n-butyl-phosphonio group, or a phosphono group di-esterified by lower alkyl, for example ethyl, the symbol X⊕ in the case of the phosphono group including in addition the cation of a strong base, especially a suitable metal ion, such as an alkali metal ion, for example a lithium, sodium or potassium ion. Preferred as the group X⊕ is, on the one hand, triphenylphosphonio and, on the other hand, diethylphosphono together with an alkali metal ion, for example a sodium ion.

In phosphonio compounds of the formula II, the negative charge is neutralised by the positively charged phosphonio group. In phosphono compounds of the formula II, the negative charge is neutralised by the cation of a strong base, which, depending upon the method of manufacture of the phosphono starting material, may be, for example, an alkali metal ion, for example a sodium, lithium or potassium ion. The phosphono starting materials are therefore used in the form of salts in the reaction. Cyclisation may take place spontaneously, that is to say during the manufacture of the starting materials, or may be effected by heating, for example in a temperature range of approximately from 30° to 160° C., preferably from approximately 50° to approximately 100° C. The reaction is preferably carried out in a suitable inert solvent, such as an aliphatic, cycloaliphatic or aromatic hydrocarbon, for example cyclohexane, benzene or toluene, a halogenated hydrocarbon, for example methylene chloride, an ether, for example diethyl ether, a cyclic ether, for example dioxan or tetrahydrofuran, a carboxylic acid amide, for example dimethylformamide, a di-lower alkyl sulphoxide, for example dimethyl sulphoxide, or a lower alkanol, for example ethanol, or in a mixture thereof, and, if necessary, in an inert gas atmosphere, for example a nitrogen atmosphere.

(c) Cyclisation of the compound of the formula III

An organic compound of trivalent phosphorus is derived, for example, from phosphorous acid and is especially an ester thereof with a lower alkanol, for example methanol or ethanol, and/or an optionally substituted aromatic hydroxy compound, for example phenol or pyrocatechol, or an amide ester thereof of the formula $P(OR_a)_2-N(R_b)_2$ in which each of $R_a$ and $R_b$, independently of the other, represents lower alkyl, for example methyl, or aryl, for example phenyl. Preferred compounds of trivalent phosphorus are tri-lower alkyl phosphites, for example trimethyl phosphite or triethyl phosphite.

The reaction is preferably carried out in an inert solvent, such as an aromatic hydrocarbon, for example toluene or xylene, an ether, for example dioxan or tetrahydrofuran, or a halogenated hydrocarbon, for example methylene chloride or chloroform, at a temperature of from approximately 20° to approximately 150° C., preferably at from approximately 40° to approximately 120° C., one molar equivalent of a compound of the formula III being reacted with two molar equivalents of the phosphorus compound. Preferably, the compound of the formula III is placed in an inert solvent and the phosphorus compound, preferably dissolved in the same inert solvent, is added dropwise over a prolonged period, for example over a period of from 2 to 4 hours.

In a preferred embodiment of the process, the starting material of the formula III is manufactured as described hereinbelow and, without being isolated from the reaction mixture, is reacted with the organic compound of trivalent phosphorus, the end products of the formula I being formed.

(d) Elimination of the radical X from compounds of the formula III'

The compounds of the formula III' are correspondingly substituted 2-thia-3-cephem-4-carboxylic acids or, especially, 2-thia-3-cephem-4-carboxylic acid 1,1-dioxides.

The elimination of sulphur from a 2-thia-3-cephem-4-carboxylic acid of the formula III' (X=S) is effected, for example, with an organic compound of trivalent phosphorus, such as, for example, one of the compounds mentioned under process (c). Suitable compounds of trivalent phosphorus are, for example, tri-lower alkyl phosphites, for example triethyl phosphite, and especially triphenylphosphine. The elimination is carried out at room temperature or at slightly elevated temperature, for example at from approximately 20° to approximately 60° C., in an inert solvent or solvent mixture, for example in a hydrocarbon, for example benzene, a chlorinated hydrocarbon, for example chloroform, or a lower alkanone, for example acetone, if necessary in an inert gas atmosphere, such as a nitrogen atmosphere.

The elimination of sulphur dioxide from a compound of the formula III' in which X represents $SO_2$ is effected, for example, in a solution containing that compound by mild to moderate heating, for example to from approximately 30° to approximately 80° C., there being suitable as solvents, especially, inert solvents, such as, for example, optionally chlorinated hydrocarbons, for example chloroform, aliphatic ethers, or aromatic hydrocarbons, for example benzene.

It is preferable to use those starting materials of the formulae I', II, III and III' which result in the compounds of the formula I mentioned at the beginning as being especially preferred.

In a resulting compound of the formula I in which one or more functional groups are protected, these groups, for example protected carboxy, hydroxy and amino groups, may be freed, optionally in stages or simultaneously, in a manner known per se by means of solvolysis, especially hydrolysis, alcoholysis or acidolysis, or by means of reduction, especially hydrogenolysis or chemical reduction.

In a compound of the formula I obtainable according to the process in which $R_2$ represents a protected carboxy group, the protected carboxy group can be freed in a manner known per se. Thus, tert.-lower alkoxycarbonyl, or lower alkoxycarbonyl substituted in the 2-position by a tri-substituted silyl group or in the 1-position by lower alkoxy, or optionally substituted diphenylmethoxycarbonyl can be converted into free carboxy, for example, by treatment with a carboxylic acid, such as formic acid or trifluoroacetic acid, optionally with the addition of a nucleophilic compound, such as phenol or anisole. Optionally substituted benzyloxycarbonyl can be cleaved, for example, by means of hydrogenolysis, that is to say by treatment with hydrogen in the presence of a metallic hydrogenation catalyst, such as a palladium catalyst. Furthermore, suitably substituted benzyloxycarbonyl, such as 4-nitrobenzyloxycarbonyl, can also be converted into free carboxy by means of chemical reduction, for example by treatment with an alkali metal dithionite, for example sodium dithionite, or with a reducing metal, for example tin, or a reducing metal salt, such as a chromium(II) salt, for example chromium(II) chloride, customarily in the presence of a hydrogen-yielding agent that together with the metal is capable of producing nascent hydrogen, such as a suitable carboxylic acid, for example a lower alkanecarboxylic acid optionally substituted, for example, by hydroxy, for example acetic acid, formic acid or glycolic acid, or an alcohol or thiol, it being preferable to add water.

The removal of an allyl protecting group can be effected, for example, by reaction with a palladium compound, for example tetrakis(triphenylphosphine)-palladium, in the presence of triphenylphosphine and with the addition of a carboxylic acid, for example 2-ethylhexanoic acid, or a salt thereof. By treatment with a reducing metal or metal salt, as described above, it is also possible to convert 2-halo-lower alkoxycarbonyl (optionally after converting a 2-bromolower alkoxycarbonyl group into a corresponding 2-iodolower alkoxycarbonyl group) or aroylmethoxycarbonyl into free carboxy, whilst aroylmethoxycarbonyl can be cleaved likewise by treatment with a nucleophilic, preferably salt-forming, reagent, such as sodium thiophenolate or sodium iodide. Substituted 2-silylethoxycarbonyl can be converted into free carboxy also by treatment with a salt of hydrofluoric acid that yields the fluoride anion, such as an alkali metal fluoride, for example sodium fluoride, in the presence of a macrocyclic polyether ("Crown ether") or with a fluoride of an organic quaternary base, such as tetralower alkylammonium fluoride, for example tetrabutylammonium fluoride. Carboxy esterified by an organic silyl or stannyl group, such as tri-lower alkylsilyl or tri-lower alkylstannyl, can be freed in customary manner by solvolysis, for example by treatment with water or an alcohol. A lower alkoxycarbonyl group substituted in the 2-position by lower alkylsulphonyl or cyano can be converted into free carboxy, for example, by treatment with a basic agent, such as an alkali metal or alkaline earth metal hydroxide or carbonate, for example sodium or potassium hydroxide or sodium or potassium carbonate.

On the other hand, also compounds of the formula I in which $R_2$ represents carboxy can be converted into compounds of the formula I in which $R_2$ represents a protected carboxy group, especially an esterified carboxy group, or an esterified carboxy group that can be cleaved under physiological conditions. Thus, the free carboxy group can be esterified, for example, by treatment with a suitable diazo compound, such as a diazolower alkane, for example diazomethane, or a phenyldiazo-lower alkane, for example diphenyldiazomethane, if necessary in the presence of a Lewis acid, such as, for example, boron trifluoride, or by reaction with an alcohol suitable for esterification in the presence of an esterifying agent, such as a carbodiimide, for example dicyclohexyl carbodiimide, and carbonyldiimidazole. Esters can also be manufactured by reaction of a salt of the acid, which salt is optionally produced in situ, with a reactive ester of an alcohol and a strong inorganic acid, such as sulphuric acid, or a strong organic sulphonic acid, such as 4-toluenesulphonic acid. Furthermore, acid halides, such as chlorides (manufactured, for example, by treatment with oxalyl chloride), activated esters (formed, for example, with N-hydroxynitrogen compounds, such as N-hydroxysuccinimide), or mixed anhydrides (obtained, for example, with haloformic acid lower alkyl esters, such as chloroformic acid ethyl ester or chloroformic acid isobutyl ester, or with haloacetic acid halides, such as trichloroacetyl chloride) can be converted into esterified carboxy groups by reaction with suitable alcohols, optionally in the presence of a base, such as pyridine.

In a compound of the formula I having an esterified carboxy group, this group can be converted into a different esterified carboxy group: for example 2-chloroethoxycarbonyl or 2-bromoethoxycarbonyl may be converted by treatment with an iodine salt, for example sodium iodide, into 2-iodoethoxycarbonyl. Furthermore, in compounds of the formula I that contain a carboxy group protected in esterified form, the carboxyprotecting group can be removed as described above, and a resulting compound of the formula I having a free carboxy group or a salt thereof can be converted by reaction with the reactive ester of a corresponding alcohol into a compound of the formula I in which $R_2$ hol into a compound of the formula I in which $R_2$ represents an esterified carboxy group that can be cleaved under physiological conditions.

In compounds of the formula I obtainable according to the process, a protected hydroxy group present in the radical $R_1$ can be converted into a free hydroxy group in a manner known per se. For example, a hydroxy group protected by a suitable acyl group or an organic silyl or stannyl group is freed in the same manner as a correspondingly protected amino group (see below); a tri-lower alkylsilyl group is removed, for example, also with tetrabutylammonium fluoride and acetic acid (under these conditions carboxy groups protected by tri-substituted silylethoxy are not cleaved). A 2-halo-lower alkyl group and an optionally substituted benzyl group are removed by reduction.

In a compound of the formula I obtainable according to the invention having a protected amino group $R_3$, this group may be converted into the free amino group in a manner known per se, for example, depending on the nature of the protecting group, preferably by means of solvolysis or reduction. For example, 2-halo-lower alkoxycarbonylamino (optionally after converting a 2-bromo-lower alkoxycarbonylamino group into a 2-iodo-lower alkoxycarbonylamino group), aroylmethoxycarbonylamino or 4-nitrobenzyloxycarbonylamino can be cleaved by treatment with a suitable chemical reducing agent, such as zinc in the presence of a suitable carboxylic acid, such as aqueous acetic acid, or by catalysis with hydrogen in the presence of a palladium catalyst. Aroylmethoxycarbonylamino may be cleaved also by treatment with a nucleophilic, preferably salt-forming, reagent, such as sodium thiophenolate, and 4-nitrobenzyloxycarbonylamino may be cleaved also by treatment with an alkali metal dithionite, for example sodium dithionite. Optionally substituted benzyloxycarbonylamino may be cleaved, for example, by means of hydrogenolysis, that is to say by treatment with hydrogen in the presence of a suitable hydrogenation catalyst, such as a palladium catalyst, and allyloxycarbonylamino by reaction with a palladium compound, for example tetrakis(triphenylphosphine)palladium, in the presence of triphenylphosphine and treatment with a carboxylic acid, for example 2-ethylhexanoic acid, or with a salt thereof. An amino group protected by an organic silyl or stannyl group can be freed, for example, by means of hydrolysis or alcoholysis, and an amino group protected by 2-halolower alkanoyl, for example 2-chloroacetyl, can be freed by treatment with thiourea in the presence of a base or with a thiolate salt, such as an alkali metal thiolate, of thiourea and subsequent solvolysis, such as alcoholysis or hydrolysis, of the resulting condensation product. An amino group protected by 2-substituted silylethoxycarbonyl can be converted into the free amino group by treatment with a salt of hydrofluoric acid that yields fluoride anions, such as an alkali metal fluoride, for example sodium fluoride, in the presence of a macrocyclic polyether ("Crown ether") or with a fluoride of an organic quaternary base, such as tetra-lower alkylammonium fluoride, for example tetraethylammonium fluoride. An amino group protected in the form of an azido or nitro group is converted into free amino, for example, by reduction, for example by catalytic hydrogenation with hydrogen in the presence of a hydrogenation catalyst, such as platinum oxide or palladium, or by treatment with zinc in the presence of an acid, such as acetic acid. An amino group protected in the form of a phthalimido group can be converted into the free amino group by reaction with hydrazine. Furthermore, an arylthioamino group can be converted into amino by treatment with a nucleophilic reagent, such as sulphurous acid.

Also, a free amino group $R_3$ can be converted in a manner known per se into a substituted amino group. Thus, for example, amino can be converted by reaction with a corresponding acyl halide, such as a chloride, into acylamino $R_3$, and with a $\beta$-dicarbonyl compound, such as a 1-lower alkanoylacetone or an acetoacetic acid lower alkyl ester, into 1-lower alkanoyl- or 1-lower alkoxycarbonylprop-1-en-2-yl-amino. The conversion of amino groups into amidino, guanidino, isourea, imidoether and imidothioether groups can be carried out, for example, in accordance with one of the processes mentioned in German Offenlegungsschrift No. 26 52 679. Thus, for example, compounds of the formula I in which $R_3$ represents amino can be converted into amidines by reaction with an imidohalide or imidoester of the formula $[(X_1, Y_1)C=X_2'H]^{\oplus}Y_2^{\ominus}$ in which $X_1$ represents hydrogen, lower alkyl, substituted lower alkyl, lower alkenyl, phenyl or monocyclic heteroaryl, $X_2$ is optionally substituted imino, Y1 is halogen, for example chlorine, or lower alkoxy, for example ethoxy, and $Y_2$ represents an anion, for example chloride, or into guanidines by reaction with a thiourea of the formula $X_1$—$C(=S)$—$X_2$ in which $X_1$ and $X_2$ represent identical or different, optionally substituted amino radicals, or with an isourea or isothiourea of the formula $(X_1Y_3)C=X_2'$ in which $Y_3$ is lower alkoxy or lower alkylthio, $X_1$ represents optionally substituted amino and $X_2'$ represents optionally substituted imino. Furthermore, a free amino group $R_3$ can be converted into an amino group mono- or di-substituted by lower alkyl. The introduction of the lower alkyl group(s) is effected, for example, by reaction with corresponding reactive lower alkyl esters, such as halides, for example chlorides or bromides, or sulphonates, for example methanesulphonates or p-toluenesulphonates, in the presence of a basic condensation agent, such as an alkali metal or alkaline earth metal hydroxide or carbonate, for example potassium hydroxide or sodium carbonate, in an inert solvent, such as a lower alkanol, at room temperature or at elevated or reduced temperature, for example at approximately from $-20°$ to $+80°$ C.

Salts of compounds of the formula I having salt-forming groups may be manufactured in a manner known per se. Thus, salts of compounds of the formula I having a free carboxy or sulpho group can be formed, for example, by treatment with metal compounds, such as alkali metal salts of suitable organic carboxylic acids, for example the sodium salt of $\alpha$-ethylcaproic acid, or with inorganic alkali metal or alkaline earth metal salts, for example sodium bicarbonate, or with ammonia or with a suitable organic amine, it being preferable to use stoichiometric amounts or only a small excess of the salt-forming agent. Acid addition salts of compounds of the formula I are obtained in customary manner, for example by treatment with a suitable acid or a suitable anion exchange reagent. Internal salts of compounds of the formula I can be formed, for example, by neutralising salts, such as acid addition salts, to the isoelectric point, for example with weak bases, or by treatment with ion exchangers.

Salts can be converted into the free compounds in customary manner; metal and ammonium salts, for example by treatment with suitable acids, and acid addition salts, for example by treatment with a suitable basic agent.

Resulting mixtures of isomeric compounds can be separated into the individual isomers according to methods known per se.

For example, a resulting racemate is allowed to react with an optically active auxiliary, the resulting mixture of two diastereoisomeric compounds is separated with the aid of suitable physico-chemical methods (for example by fractional crystallisation, adsorption chromatography) and the individual diastereoisomeric compounds are then separated into the optically active compounds.

Racemates that are especially suitable for separation into the antipodes are those which contain an acidic group, such as, for example, racemates of compounds of the formula I in which $R_2$ represents carboxy. These acidic racemates can be reacted with optically active bases, for example esters of optically active amino acids, or (−)-brucine, (+)-quinidine, (−)-quinine, (+)-cinchonine, (+)-dehydroabietylamine, (+)- and (−)-ephedrin, (+)- and (−)-1-phenylethylamine or their N-mono- or N,N-di-alkylated derivatives, to form mixtures consisting of two diastereoisomeric salts.

In racemates that contain carboxy groups, the carboxy group can also be esterified by an optically active alcohol, such as (−)-menthol, (+)-borneol, (+)- or (−)-2-octanol, whereupon, when isolation of the desired diastereoisomer is complete, the carboxy group is freed.

For separation of the racemates, a hydroxy group present can also be esterified by optically active acids or reactive functional derivatives thereof, diastereoisomeric esters being formed. Such acids are, for example, (−)-abietic acid, D(+)- and L(−)-malic acid, N-acylated optically active amino acids, (+)- and (−)-camphanic acid, (+)- and (−)-ketopinic acid, L(+)-ascorbic acid, (+)-camphoric acid, (+)-camphor-10-sulphonic acid($\beta$), (+)- or (−)-$\alpha$-bromocamphor-$\pi$-sulphonic acid, D(−)-quinic acid, D(−)-isoascorbic acid, D(−)- and L(+)-mandelic acid, (+)-1-menthoxyacetic acid, D(−)- and L(+)-tartaric acid and the di-O-benzoyl and di-O-p-toluoyl derivatives thereof.

By reaction with optically active isocyanates, such as with (+)- or (−)-1-phenylethyl isocyanate, it is possible to convert compounds of the formula (I) in which $R_2$ represents protected carboxy and $R_1$ represents lower alkyl substituted by hydroxy into a mixture of diastereoisomeric urethanes.

Basic racemates, for example compounds of the formula I in which $R_3$ is amino, can form diastereoisomeric salts with the mentioned optically active acids.

The splitting up of the separated diastereoisomers into the optically active compounds of the formula I is also effected according to customary methods. The acids or the bases are freed from the salts, for example, by treatment with acids or bases that are stronger than those originally used. The desired optically active compounds are obtained from the esters and urethanes, for example, after alkaline hydrolysis or after reduction with a complex hydride, such as lithium aluminium hydride.

A further method of separating the racemates comprises chromatography on optically active adsorption layers, for example on cane sugar.

According to a third method, the racemates can be dissolved in optically active solvents and the more sparingly soluble optical antipode can be crystallised out.

A fourth method utilises the different reactivities of the optical antipodes with respect to biological material, such as micro-organisms or isolated enzymes.

According to a fifth method, the racemates are dissolved and one of the optical antipodes is crystallised out by inoculation with a small quantity of an optically active product obtained according to the above methods.

The separation of the racemates into the optical antipodes can be carried out at any stage of the process, that is to say, for example, even at the stage of the starting compounds of the formula I', II, III or III' or at any stage of the process for the manufacture of the starting compounds of the formula I', II, III or III' that is described hereinafter.

In all subsequent conversions of resulting compounds of the formula I, those reactions are preferred which take place under alkaline or, especially, neutral conditions.

The process also includes those embodiments according to which compounds formed as intermediates are used as starting materials and the remaining process steps are carried out with them, or the process is interrupted at any stage. Furthermore, starting materials can be used in the form of derivatives or can be manufactured in situ, optionally under the reaction conditions.

The starting compounds of the formulae II and III can be manufactured as indicated in the following reaction scheme I.

Reaction Scheme I

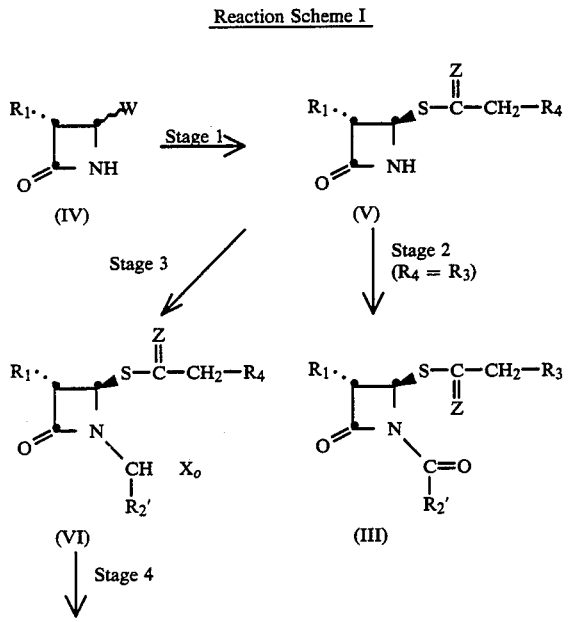

-continued
Reaction Scheme I

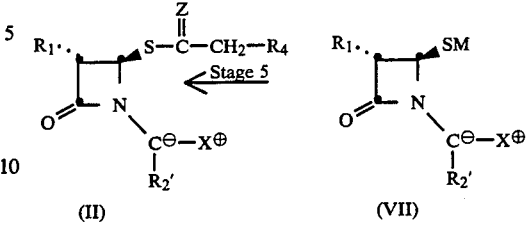

In the compounds of the formulae II, V and VI, $R_4$ is either the radical $R_3$ or a group Q.

Stage 1

A thioazetidinone of the formula V is obtained by reacting a compound of the formula IV with a compound that introduces the radical $-S-C(=Z)-CH_2-R_4$.

In a starting material of the formula IV, W is a nucleofugal radical that can be replaced by the group $-S-C(=Z)-CH_2-R_4$. Such radicals W are, for example, acyloxy radicals, sulphonyl radicals $R_o-SO_2-$ in which $R_o$ is an organic radical, or azido or halogen. In an acyloxy radical W, acyl is, for example, the radical of an organic carboxylic acid, and represents, for example, lower alkanoyl, for example acetyl or propionyl, optionally substituted benzoyl, for example benzoyl or 2,4-dinitrobenzoyl, or phenyl-lower alkanoyl, for example phenylacetyl. In a sulphonyl radical $R_o-SO_2-$, $R_o$ is, for example, lower alkyl optionradical ally substituted by hydroxy, such as methyl, ethyl, tert.-butyl, 1-hydroxyprop-2-yl, 1-hydroxy-2-methylprop-2-yl or 2-hydroxyethyl, benzyl or optionally substituted phenyl, such as phenyl, 4-bromophenyl or 4-methylphenyl. A halogen radical W is, for example, bromine, iodine or, especially, chlorine. W is preferably methyl-, tert.-butyl- or 2-hydroxyethylsulphonyl, acetoxy or chlorine.

A compound that introduces the radical $-S-C(=Z)-CH_2-R_4$ is, for example, an acid of the formula $R_4-CH_2-C(=Z)-SH$ or especially a salt, for example an alkali metal salt, such as the sodium or potassium salt, thereof. The substitution can be carried out in an organic solvent, such as a lower alkanol, for example methanol or ethanol, a lower alkanone, for example acetone, a lower alkanecarboxylic acid amide, for example dimethylformamide, a cyclic ether, for example tetrahydrofuran or dioxan, or in a similar inert solvent. The reaction is customarily carried out at room temperature but may also be carried out at elevated or reduced temperature, for example at from approximately 0° to approximately 40° C. The reaction can be accelerated by adding a salt of hydriodic acid or of thiocyanic acid, for example an alkali metal salt, such as the sodium salt.

The group $-S-C(=Z)-CH_2-R_4$ being introduced is directed by the radical $R_1$ preferentially into the trans-position. It is therefore possible to use both (3S,4R)- and (3S,4S)-configured starting compounds of the formula IV. Although predominantly the transisomers are formed, occasionally, small amounts of the cis-isomers may also be produced. The cis-isomers are separated off according to conventional methods, as described above, especially by chromatography and/or by crystallisation.

Suitable starting compounds of the formula IV are known, for example from European Patent Application No. 82113, German Offenlegungsschrift No. 3013997 or German Offenlegungsschrift No. 3224055, or can be manufactured in an analogous manner. They can also be manufactured according to the processes described in the Examples.

Stage 2

A starting compound of the formula (III) is obtained by treating an azetidinone of the formula (V) in which $R_4$ represents the radical $R_3$ with an acid of the formula $R_2'$—COOH or especially a reactive derivative, such as an ester or acid halide, for example the acid chloride, thereof at a temperature of from −20° to 80° C., preferably from −20° to 40° C., in an inert solvent, such as one of those mentioned for the reaction of compounds of the formula III to form compounds of the formula I. When using an acid halide, the operation is preferably carried out in the presence of an acid-binding agent, such as a tertiary aliphatic amine, for example triethylamine or diisopropylethylamine ("Hünig base"), an aromatic amine, for example pyridine, or especially an alkali metal or alkaline earth metal carbonate or bicarbonate, for example potassium carbonate or calcium carbonate.

Stage 3

Compounds of the formula VI in which $X_o$ represents a reactive esterified hydroxy group, especially halogen, for example chlorine or bromine, or organic sulphonyloxy, for example lower alkanesulphonyloxy, such as methanesulphonyloxy, or arenesulphonyloxy, for example benzene- or 4-methylbenzene-sulphonyloxy, are manufactured by reacting a compound of the formula V with a glyoxylic acid compound of the formula OHC—$R_2'$ or with a suitable derivative thereof, such as a hydrate, hemihydrate or hemiacetal, for example a hemiacetal with a lower alkanol, for example methanol or ethanol, and, in a resulting compound of the formula VI in which $X_o$ represents hydroxy, converting the hydroxy group into a reactive esterified hydroxy group.

The compounds of the formula VI are usually obtained in the form of a mixture of the two isomers [with respect to the —CH($R_2'$) ～～ $X_o$ grouping]. It is also possible, however, to isolate the pure isomers thereof, for example by chromatography.

The addition of the glyoxylic acid ester compound to the nitrogen atom of the lactam ring in the compound of the formula V is effected at room temperature or, if necessary, while heating, for example at approximately 100° C., and in the absence of an actual condensation agent. When using the hydrate of the glyoxylic acid compound, water is formed which, if necessary, is removed by distillation, for example azeotropic distillation, or by using a suitable dehydrating agent, such as a molecular sieve. The operation is preferably carried out in the presence of a suitable solvent, such as, for example, dioxan, toluene or dimethylformamide, or a solvent mixture and, if desired or necessary, in the atmosphere of an inert gas, such as nitrogen.

The conversion of a hydroxy group $X_o$ into a reactive esterified hydroxy group $X_o$ in a compound of the formula VI is carried out by treatment with a suitable esterification agent, for example with a thionyl halide, for example the chloride, a phosphorus oxyhalide, especially the oxychloride, a halophosphonium halide, such as triphenylphosphonium dibromide or dichloride, or a suitable organic sulphonic acid halide, such as the chloride, preferably in the presence of a basic agent, especially an organic basic agent, such as an aliphatic tertiary amine, for example triethylamine or diisopropylamine, or a heterocyclic base of the pyridine type, for example pyridine or collidine. The operation is preferably carried out in the presence of a suitable solvent, for example dioxan or tetrahydrofuran, or a solvent mixture, if necessary while cooling, for example at from approximately −30° to approximately 30° C., and optionally in the atmosphere of an inert gas, such as nitrogen.

Stage 4

The starting material of the formula (II) is obtained by treating a compound of the formula (VI) with a suitable phosphine compound, such as a tri-lower alkylphosphine, for example tri-n-butylphosphine, or a triarylphosphine, for example triphenylphosphine, or with a suitable phosphite compound, such as a tri-lower alkyl phosphite, for example triethyl phosphite, or an alkali metal di-lower alkyl phosphite, for example an alkali metal diethyl phosphite.

The above reaction is preferably carried out in the presence of a suitable inert solvent, such as a hydrocarbon, for example cyclohexane or benzene, or an ether, for example dioxan, or a solvent mixture. Depending upon the reactivity, the operation is carried out while cooling or at elevated temperature, at approximately from −10° to +100° C., preferably at approximately from 20° to 80° C., and/or in the atmosphere of an inert gas, such as nitrogen. In order to prevent oxidative processes taking place, catalytic amounts of an antioxidant, for example hydroquinone, can be added.

The reaction is customarily carried out in the presence of a basic agent, such as an organic base, for example an amine, such as triethylamine, diisopropylethylamine, pyridine, lutidine or "polystyrene Hünig base", or an inorganic base, for example an alkali metal carbonate, for example sodium or potassium carbonate, the initially produced phosphonium salt of the formula

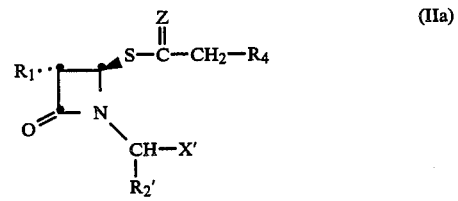 (IIa)

in which X′ represents a phosphono group or a phosphonio group together with an anion, which, depending on the meaning of the radical $X_o$, may be, for example, chloride, being converted into the ylide starting material of the formula II. It is also possible, however, to carry out the reaction in the absence of a base and to isolate a compound of the formula (IIa), especially a corresponding phosphono compound, and convert that compound into the starting material of the formula II in situ during the manufacture of the end products of the formula (I).

Stage 5

A compound of the formula (II) can furthermore be obtained by treating a mercaptide of the formula (VII), in which M represents a metal cation, with an acylating agent that introduces the radical R$_4$—CH$_2$—C(=Z)—.

In the starting material of the formula (VII), the metal cation M is, for example, a cation of the formula M+ or M$^{2+}$/2 in which M+ represents especially a silver cation and M$^{2+}$ represents especially the divalent cation of a suitable transition metal, for example copper, lead or mercury.

An acylating agent that introduces the radical R$_4$—CH$_2$—C(=Z)— is, for example, the acid R$_4$—CH$_2$—C(=Z)—OH or especially a reactive functional derivative thereof, such as an acid halide, for example chloride or bromide, or an azide or anhydride thereof.

If a reactive functional derivative of the acid of the formula R$_4$—CH$_2$—C(=Z)—OH, for example the acid chloride, is used, the acylation is carried out in an inert solvent, such as a chlorinated hydrocarbon, for example methylene chloride, or an ether, for example diethyl ether or dioxan, at room temperature or while heating or cooling, for example in a temperature range of from approximately $-50°$ to approximately $+60°$ C., especially from approximately $-30°$ to approximately $+20°$ C.

The starting compounds of the formula (VII) can be manufactured, for example, by converting an azetidinone of the formula

(IV)

by reaction with an alkali metal salt, for example the sodium salt, of a thio-lower alkanecarboxylic acid, for example thioacetic acid, or of triphenylmethyl mercaptan, into a compound of the formula

(VIII)

in which W' represents triphenylmethylthio or lower alkanoylthio, for example acetylthio, converting this compound, analogously to the process described in reaction stages 3 and 4, into a compound of the formula

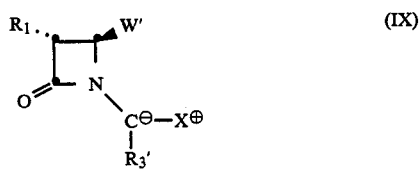

(IX)

and reacting this in the presence of a base, for example pyridine or tri-n-butylamine, in a suitable solvent, for example diethyl ether or methanol, with a salt of the formula MA in which M has the meaning given above but represents especially a silver cation, and A represents a customary anion that promotes the solubility of the salt MA in the chosen solvent, for example the nitrate, acetate or fluoride anion.

The ylides of the formula II can be used directly in the cyclisation reaction for the manufacture of the end products of the formula I. It is also possible, however, in compounds of the formula II in which R$_1$ is lower alkyl substituted by a protected hydroxy group, for example a protected hydroxy group that can readily be cleaved by hydrolysis, such as tri-substituted silyloxy, first to remove the hydroxy-protecting group and then to use the resulting compound of the formula II in which R$_1$ represents lower alkyl substituted by hydroxy in the cyclisation reaction.

The starting compounds of the formula III' in which X represents the group —S— are known (for example from Belgian Patent Specification No. 898382 and from Tetrahedron Letters 1983, 1631–1634) or can be manufactured in an analogous manner. Compounds of the formula III' in which X represents a sulphonyl group —SO$_2$— are manufactured by reacting a compound of the formula

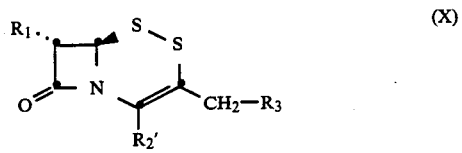

(X)

in which R$_1$ and R$_3$ have the meanings given under formula I and R$_2$' is protected carboxy, with an aliphatic or aromatic percarboxylic acid, for example peracetic acid, m-chloroperbenzoic acid or monoperphthalic acid, in an inert solvent or solvent mixture, for example in a halogenated hydrocarbon, for example chloroform, an ether or an aromatic hydrocarbon, for example benzene, at a temperature of from approximately 0° to approximately 60° C.

The functional groups present in the starting materials and intermediates of the formulae I', II, III, III' and IV-X may be protected by conventional protecting groups in a manner analogous to that described for the end products of the formula I.

In compounds of the formula (II)–(X), functional groups may be converted into protected functional groups, or protected functional groups may be converted into the free groups or into differently protected groups. Furthermore, in compounds of the formulae (II), (III), (III'), (V) and (VI), a radical R$_3$ may be converted into a different radical R$_3$. In these conversions it is possible, taking into consideration the further substituents present in the molecules, to use the same methods as those indicated in the corresponding conversions into the compounds of the formula (I).

It is also possible to carry out the process described in Reaction Scheme I for the manufacture of compounds of the formulae (I'), (II), (III) and (V)–(VII) and the processes indicated for the manufacture of the end products of the formula (I) with optically inactive compounds and to isolate the optically active compounds according to the present invention from a resulting diastereoisomeric mixture or racemate, as described above, at any desired stage of the process.

The invention relates also to the novel starting compounds and to novel intermediates which are obtainable according to the process, such as those of the formulae (II), (III), (V)–(VII), (IX) and (X), and to the processes indicated for the manufacture thereof.

The starting materials used and reaction conditions chosen are preferably those which result in the compounds described hereinbefore as being especially preferred.

The compounds of the formula I have valuable pharmacological properties or can be used as intermediates for the manufacture of such compounds having valuable pharmacological properties. Compounds of the formula I in which $R_1$ represents hydroxy-lower alkyl, $R_2$ represents carboxy or an esterified carboxy group that can be cleaved under physiological conditions, and $R_3$ represents amino, lower alkylamino, di-lower alkylamino, or methyleneamino which is substituted as indicated, and pharmacologically acceptable salts of such compounds having salt-forming groups have anti-bacterial activity. For example, they are effective in vitro against gram-positive and gram-negative cocci, for example *Staphylococcus aureus, Streptococcus pyogenes, Streptococcus pneumoniae, Streptococcus faecalis, Neisseria meningitidis* and *Neisseria gonorrhoeae*, and against enterobacteria, for example *Escherichia coli, Proteus mirabilis* and *Klebsiella pneumoniae*, against *Haemophilus influenzae* and *Pseudomonas aeruginosa*, and anaerobes, for example Bacteroides sp. and Clostridium sp., in minimum concentrations of from approximately 0.02 to approximately 64 μg/ml. In vivo, in the case of systemic infection of mice, for example by *Staphylococcus aureus, Escherichia coli* or *Streptococcus pyogenes*, on subcutaneous or oral administration $ED_{50}$ values of from approximately 0.3 to approximately 30 mg/kg are obtained.

Thus, (5R,6S)-2-aminomethyl-6-[(1'R)-1-hydroxyethyl]-2-penem-3-carboxylic acid (compound A) and (5R,6S)-2-aminomethyl-6-hydroxymethyl-2-penem-3-carboxylic acid (compound C) exhibit in vitro, in comparison with the racemic (1'R,5R,6S+1'S,5S,6R)-2-aminomethyl-6-(1'hydroxyethyl)-2-penem-3-carboxylic acid (compound B) known from U.S. Pat. No. 4,272,437, the following superior activities:

TABLE 1

Antibiotic activity of compounds of the formula I and of the known comparison compound B in vitro

| | in vitro MIC (μg/ml) | | |
|---|---|---|---|
| microorganism | compound A | compound B | compound C |
| *Staphylococcus aureus* 10 B | 0.05 | 0.1 | 0.2 |
| *Staphylococcus aureus* 2999i+p+ | 0.05 | 0.2 | 0.5 |
| *Staphylococcus aureus* A 124 | 0.1 | 0.2 | 1 |
| *Staphylococcus aureus* Wood 46 | 0.05 | 0.1 | 0.2 |
| *Streptococcus pyogenes* Aronson 1129 | 0.2 | 0.5 | 2 |
| *Streptococcus pneumoniae* III/84 | 0.1 | 0.2 | 0.5 |
| *Neisseria meningitidis* 1316 | 0.5 | 1 | 1 |
| *Neisseria gonorrhoeae* 1317/4 | 0.5 | 1 | 1 |
| *Haemophilus influenzae* NCTC 4560 | 1 | 2 | 1 |
| *Escherichia coli* 205 | 2 | 8 | 1 |
| *Escherichia coli* 205 R + TEM | 4 | 8 | 2 |
| *Escherichia coli* 16 | 4 | 8 | 2 |
| *Escherichia coli* 2018 | 2 | 4 | 1 |
| *Escherichia coli* UB 1005 | 4 | 16 | 2 |
| *Escherichia coli* DC 2 | 8 | 16 | 4 |
| *Escherichia coli* B-1385 | 4 | 8 | 2 |
| *Klebsiella pneumoniae* 327 | 2 | 4 | 1 |
| *Serratia marcescens* 344 | 4 | 8 | 2 |
| *Enterobacter cloacae* P 99 | 4 | 8 | 4 |
| *Enterobacter cloacae* ATCC 13047 | 4 | 16 | 4 |
| *Proteus mirabilis* 774 | 1 | 4 | 1 |
| *Proteus mirabilis* 1219 | 2 | 8 | 4 |
| *Proteus rettgeri* 856 | 0.5 | 1 | 0.5 |
| *Proteus morganii* 2359 | 0.5 | 2 | 1 |
| *Proteus morganii* 1518 | 2 | 4 | 2 |
| *Pseudomonas aeruginosa* ATCC 12055 | 0.05 | 0.1 | 0.2 |

TABLE 1-continued

Antibiotic activity of compounds of the formula I and of the known comparison compound B in vitro

| | in vitro MIC (μg/ml) | | |
|---|---|---|---|
| microorganism | compound A | compound B | compound C |
| *Pseudomonas aeruginosa* K 799/61 | 0.1 | 0.2 | 0.5 |
| *Pseudomonas aeruginosa* 143738R | 0.5 | 2 | 2 |
| *Clostridium perfringens* | 2 | 4 | 32 |
| *Bacteroides fragilis* L 01 | 0.5 | 1 | 2 |

Compared with the corresponding known racemate (compound B), the optically active compound A according to the invention exhibits, in all the strains tested, an activity that is greater by a factor of 2 to 4. The optically active compound C according to the invention exhibits, in all the strains tested, a remarkably constant activity and is superior to the known racemic homologue (compound B), especially in the gram-negative area, by a factor of 2 to 8.

The stability of compounds A, B and C towards the enzyme dehydropeptidase from human kidneys is as follows (expressed in half-life periods $t_{\frac{1}{2}}$):

| | $t_{\frac{1}{2}}$ (hours) |
|---|---|
| compound A | 6.75 |
| compound B | 2.20 |
| compound C | 5.50 |

Compared with the prior-described racemate (compound B), the compounds A and C according to the invention surprisingly have a considerably greater half-life period under the action of renal dehydropeptidase.

The novel compounds can therefore be used as orally or parenterally administrable antibacterial antibiotics, for example in the form of corresponding pharmaceutical preparations, for the treatment of infections.

Compounds of the formula I in which at least one of the functional groups present is in protected form, a protected carboxy group being other than an esterified carboxy group that can be cleaved under physiological conditions, can be used as intermediates for the manufacture of the above-mentioned pharmacologically active compounds of the formula I.

The pharmacologically acceptable compounds of the present invention can be used, for example, for the manufacture of pharmaceutical preparations that contain an effective amount of the active ingredient together or in admixture with inorganic or organic, solid or liquid, pharmaceutically acceptable carriers that are suitable for oral or for parenteral, that is to say intramuscular, subcutaneous or intraperitoneal, administration.

For oral administration there are used tablets or gelatine capsules that contain the active ingredient together with diluents, for example lactose, dextrose, sucrose, mannitol, sorbitol, cellulose and/or glycine, and lubricants, for example silica, talc, stearic acid or salts thereof, such as magnesium or calcium stearate, and/or polyethylene glycol; tablets also contain binders, for example magnesium aluminium silicate, starches, such as corn, wheat, rice or arrowroot starch, gelatine, tragacanth, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures or adsorbents, colourings, flavourings or sweeteners.

For parenteral administration there are suitable especially infusion solutions, preferably isotonic aqueous solutions or suspensions, it being possible to prepare these before use, for example from lyophilised preparations that contain the active ingredient on its own or together with a carrier, for example mannitol. Such preparations may be sterilised and/or contain adjuncts, for example preservatives, stabilisers, wetting agents and/or emulsifiers, solubilisers, salts for regulating the osmotic pressure and/or buffers.

The present pharmaceutical preparations, which, if desired, may contain other pharmacologically valuable substances, are manufactured in a manner known per se, for example by means of conventional mixing, dissolving or lyophilising processes, and contain from approximately 0.1% to 100%, especially from approximately 1% to approximately 50% or, in the case of lyophilisates, up to 100%, active ingredient.

Depending upon the type of infection and the condition of the infected organism, the daily dose used for the treatment of a warm-blooded animal (human or animal) weighing approximately 70 kg is from 125 mg to approximately 5 g.

The following Examples serve to illustrate the invention. Temperatures are given in degrees Centigrade.

The following abbreviations are used in the Examples:

TLC: thin-layer chromatograph
IR: infra-red spectrum
UV: ultraviolet spectrum
NMR: nuclear resonance spectrum
DBU: 1,5-diazabicyclo[5.4.0]undec-5-ene
THF: tetrahydrofuran
DMF: dimethylformamide.

EXPERIMENTAL PART

EXAMPLE 1

(5R,6S)-2-(allyloxycarbonylaminomethyl)-6-(tert.-butyldimethylsilyloxymethyl)-2-penem-3-carboxylic acid allyl ester A solution of 3.05 g of 2-[(3S,4R)-3-(tert.-butyldimethylsilyloxymethyl)-4-(allyloxycarbonylaminoacetylthio)-2-oxo-azetidin-1-yl]-2-triphenylphosphoranylideneacetic acid allyl ester in 200 ml of absolute toluene is stirred at reflux temperature for 90 minutes under an argon atmosphere. The solvent is then concentrated by evaporation and the crude product is purified by chromatography over silica gel. (Eluant toluene/ethyl acetate 9:1). IR ($CH_2Cl_2$) : 3435; 1785; 1710; 1580 $cm^{-1}$.

The starting material is manufactured as follows:

(a)
(3S,4R)-3-(tert.-butyldimethylsilyloxymethyl)-4-triphenylmethylthio-azetidin-2-one At 0°, 12.5 g of triphenylmethyl mercaptan are suspended in 70 ml of methanol and there is added in portions, over a period of 10 minutes, a total of 2.2 g of a 55% sodium hydride suspension in oil. There is then added dropwise, over a period of 30 minutes, an emulsion of 11.1 g of (3S,4R)-3-(tert.-butyldimethylsilyloxymethyl)-4-methylsulphonylazetidin-2-one (European Patent Application No. 82113) in 70 ml of acetone and 70 ml of water. After being stirred for 30 minutes at 0° and for 1 hour at room temperature, the reaction mixture is concentrated in a rotary evaporator, methylene chloride is added thereto, and the aqueous phase is separated off. The organic solution is washed with brine and dried over sodium sulphate. After concentration, the crude title compound is purified by chromatography over silica gel (eluant toluene/ethyl acetate 19:1). TLC (toluene/ethyl acetate 19:1): $R_f=0.64$; IR (methylene chloride): 3390, 1760, 1117, 835 $cm^{-1}$.

(b)
2-[(3S,4R)-3-tert.-butyldimethylsilyloxymethyl)-4-triphenylmethylthio-2-oxo-azetidin-1-yl]-2-hydroxyacetic acid allyl ester 27 g of molecular sieve (4Å) are added to 8.4 g of (3S,4R)-3-(tert.-butyldimethylsilyloxymethyl)-4-triphenylmethylthio-azetidin-2-one and 8.23 g of glyoxylic acid allyl ester ethyl hemiacetal in 170 ml of absolute toluene and the whole is stirred at 55° for 10 hours. After being filtered off and concentrated in a rotary evaporator under reduced pressure, the crude product is purified by chromatography over silica gel (eluant toluene/ethyl acetate 95:5); TLC (silica gel, toluene/ethyl acetate 10:1): $R_f=0.37$ and 0.27; IR ($CH_2Cl_2$): 3520, 1760, 1745 $cm^{-1}$.

(c)
2-[(3S,4R)-3-(tert.-butyldimethylsilyloxymethyl)-4-triphenylmethylthio-2-oxo-azetidin-1-yl]-2-triphenylphosphoranylideneacetic acid allyl ester To a solution of 604 mg of 2-[(3S,4R)-3-(tert.-butyldimethylsilyloxymethyl)-4-triphenylmethylthio-2-oxo-azetidin-1-yl]-2-hydroxyacetic acid allyl ester in 5 ml of tetrahydrofuran there are added in succession, over a period of 5 minutes, while stirring at −15°, 80 μl of thionyl chloride and 88 μl of pyridine. The white suspension is then stirred for 1 hour at −10° and filtered over Hyflo. After washing the residue with toluene, concentration is carried out in a rotary evaporator. The residue is dissolved in 3 ml of dioxan, and 293 mg of triphenylphosphine and 0.13 ml of 2,6-lutidine are added thereto and the whole is stirred for 2 hours at a bath temperature of 115°. The mixture is filtered over Hyflo and the residue is then washed with toluene. The combined filtrates are concentrated by evaporation. Chromatography of the residue over silica gel yields the pure product (eluant toluene/ethyl acetate 95:5); TLC (silica gel, toluene/ethyl acetate 1:1): $R_f=0.18$; IR ($CH_2Cl_2$) 1745, 1605 $cm^{-1}$.

(d) the silver salt of
2-[(3S,4R)-3-(tert.-butyldimethylsilyloxymethyl)-4-mercapto-2-oxo-azetidin-1-yl]-2-triphenylphosphoranylideneacetic acid allyl ester 7.5 g of 2-[(3S,4R)-3-(tert.-butyldimethylsilyloxymethyl)-4-triphenylmethylthio-2-oxo-azetidin-1-yl]-2-triphenylphosphoranylideneacetic acid allyl ester are introduced into 87 ml of ether and, at room temperature, 70 ml of a 0.5M aqueous silver nitrate solution are added thereto. There is then added dropwise a mixture of 3.6 ml of tributylamine, 0.18 ml of trifluoroacetic acid and 25 ml of ether and the reaction mixture is stirred for a further 20 minutes. The solid material is then filtered off with suction and washed with ether, water and ether. For purification, the solid material is made into a slurry in 40 ml of ether and 40 ml of water, filtered off with suction and dried. IR ($CH_2Cl_2$): 1760, 1620 $cm^{-1}$.

(e) 2-[(3S,4R)-3-(tert.-butyldimethylsilyloxymethyl)-4-(allyloxycarbonylaminoacetylthio)-2-oxo-azetidin-1-yl]-2-triphenylphosphoranylideneacetic acid allyl ester To 5 g of the silver salt of 2-[(3S,4R)-3-(tert.-butyldimethylsilyloxymethyl)-4-mercapto-2-oxo-azetidin-1-yl]-2-triphenylphosphoranylideneacetic acid allyl ester in 20 ml of absolute methylene chloride there are added 1.7 ml of pyridine and then, at 0°, dropwise, a mixture of 1.87 g of allyloxycarbonylaminoacetyl chloride and 10 ml of absolute methylene chloride. After stirring for 30 minutes, the solid material is filtered off over Hyflo and the filtrate is washed with aqueous $NaHCO_3$ solution and then with brine. After drying over $Na_2SO_4$, concentration is carried out in vacuo. The residue is purified by chromatography over silica gel (eluant toluene-/ethyl acetate 4:1). IR ($CH_2Cl_2$): 3435, 1750, 1735, 1695, 1615 $cm^{-1}$.

The starting material allyloxycarbonylaminoacetyl chloride can be manufactured as follows:

(ea) allyloxycarbonylaminoacetic acid 12 ml of chloroformic acid allyl ester are added dropwise at 0° to a solution of 7.51 g of glycine in 20 ml of water and 44 ml of 5N NaOH solution. The suspension is then stirred for 16 hours at room temperature. After removal of the insoluble material by filtration, the filtrate is diluted with 100 ml of water and washed twice with $CH_2Cl_2$. The aqueous phase is adjusted to pH 2 with 4N HCl and extracted twice with $CH_2Cl_2$. The combined organic extracts are washed once with brine, dried over $MgSO_4$ and concentrated by evaporation to form the white crystals of the title compound. IR in $CH_2Cl_2$: 3450, 1715 $cm^{-1}$.

(eb) allyloxycarbonylaminoacetyl chloride 5.7 ml of thionyl chloride are added at 0° to 3.18 g of allyloxycarbonylaminoacetic acid. At the same temperature, the mixture is then stirred under a protective gas for 2 hours. It is then diluted with absolute toluene and concentrated in a rotary evaporator. IR ($CH_2Cl_2$): 3435, 1800, 1725 $cm^{-1}$.

Example 2

(5R,6S)-2-(allyloxycarbonylaminomethyl)-6-hydroxymethyl-2-penem-3-carboxylic acid allyl ester 1.83 ml of acetic acid and 80 ml of a 0.1N tetrabutylammonium fluoride solution in THF are added in succession to a solution of 1.79 g of (5R,6S)-2-(allyloxycarbonylaminomethyl)-6-(tert.-butyldimethylsilyloxymethyl)-2-penem-3-carboxylic acid allyl ester in 50 ml of absolute THF. After stirring for 4.5 hours, the mixture is diluted with 1.4 liters of $CH_2Cl_2$ and washed with 200 ml of a saturated $NaHCO_3$ in $H_2O$ solution. The organic phase is then washed with brine, dried over $MgSO_4$ and, after filtration, concentrated by evaporation. The crude product is purified by chromatography over silica gel (eluant: from toluene/ethyl acetate 1:1 to absolute ethyl acetate). IR ($CH_2Cl_2$): 3600, 3435, 1785, 1695, 1615 $cm^{-1}$.

Example 3

(5R,6S)-2-aminomethyl-6-hydroxymethyl-2-penem-3-carboxylic acid

At −10°, 60 mg of tetrakis-(triphenylphosphine)palladium and then 1 ml of tributyltin hydride are added to a solution of 550 mg of (5R,6S)-2-allyloxycarbonylaminomethyl- 6-hydroxymethyl-2-penem-3-carboxylic acid allyl ester in 20 ml of absolute THF. After stirring for 20 minutes at −10°, 0.2 ml of acetic acid is added and, after removing the cooling bath, the reaction mixture is stirred for a further 30 minutes. After concentration in a rotary evaporator, the residue is taken up in water/ethyl acetate, the aqueous phase is separated off and the organic phase is extracted three times more with water. After brief concentration in a rotary evaporator, the combined aqueous phases are lyophilised. UV (phosphate buffer pH 7.4): $\lambda_{max}$=309 nm.

Example 4

(5R,6S)-2-(allyloxycarbonylaminomethyl)-6-[(1'R)-1-allyloxycarbonyloxyethyl]-2-penem-3-carboxylic acid allyl ester A solution of 2.42 g of 2-[(3S,4R)-3-[(1'R)-1-allyloxycarbonyloxyethyl]-4-(allyloxycarbonylaminoacetylthio)-2-oxo-azetidin-1-yl]-2-triphenylphosphoranylideneacetic acid allyl ester in 300 ml of absolute toluene is stirred at reflux temperature for 24 hours under an argon atmosphere. The solvent is then concentrated by evaporation and the crude product is purified by chromatography over silica gel. (Eluant toluene/ethyl acetate 9:1). IR ($CH_2Cl_2$): 3435, 1790, 1740, 1720, 1580 $cm^{-1}$.

The starting material is manufactured as follows:

(a) N-p-methoxybenzyl-N-tert.-butylthiomethylammonium chloride

To a solution of 10.69 g (23.9 mmol) of 1,3,5-tris(p-methoxybenzyl)-hexahydro-1,3,5-triazine, which can be manufactured in a manner analogous to that prescribed in German Offenlegungsschrift DE-A-No. 2,431,862, in 170 ml of acetonitrile there are added in succession, at room temperature, a solution of 2.88 g (78.8 mmol) of hydrogen chloride in 20 ml of acetonitrile and 6.45 g (71.66 mmol) of tert.-butyl mercaptan. The mixture is stirred for 22 hours. The undissolved material is filtered off with suction and the filtrate is concentrated under reduced pressure. A crystalline residue is obtained which is stirred with ether and filtered off with suction. M.p. 142°.

(b) (2S,3R)-N-p-methoxybenzyl-N-tert.-butylthiomethyl-2-bromo-3-hydroxybutyramide To a solution of 1.83 g (10 mmol) of (2S,3R)-2-bromo-3-hydroxybutyric acid, manufactured analogously to a method prescribed by Shimohigashi et al., Bull. Chem. Soc. Japan 52, 949 (1979), there are added in succession, at room temperature, 2.76 g (10 mmol) of N-p-methoxybenzyl-N-tert.-butylthiomethylammonium chloride, 2.06 g (10 mmol) of dicyclohexyl carbodiimide and, dropwise, 1.40 ml (10 mmol) of triethylamine. The resulting reaction mixture is stirred at room temperature for 2 hours. The dicyclohexylurea which has separated out is filtered off with suction, and the filtrate is diluted with methylene chloride and washed with water and phosphate buffer solution of pH 8. The organic phase is dried over sodium sulphate and concentrated by evaporation, and the oily residue is chromatographed over silica gel with toluene/ethyl acetate. The title compound is obtained in the form of a colourless, viscous oil. R$_f$ (toluene/ethyl acetate 1:1): 0.55; IR (in methylene chloride): 3550–3200, 2950–2850, 1632, 1608, 1508, 1457, 1438, 1407, 1360, 1242, 1202, 1175, 1150, 1028 cm$^{-1}$.

(c)
(2S,3R)-N-p-methoxybenzyl-N-tert.-butylsulphonyl-methyl-2-bromo-3-hydroxybutyramide 2.06 g (approximately 2.2 equivalents) of 90% m-chloroperbenzoic acid are added at −14°, while stirring, to a solution of 1.97 g (4.89 mmol) of (2S,3R)-N-p-methoxybenzyl-N-tert.-butylthiomethyl-2-bromo-3-hydroxybutyramide in 50 ml of methylene chloride. The reaction mixture is stirred at 0° for 80 minutes. The m-chlorobenzoic acid which has separated out is filtered off and the filtrate is diluted with methylene chloride and shaken in succession with 3% aqueous sodium bisulphite solution and 8% aqueous sodium bicarbonate solution. The organic phase is dried over sodium sulphate and concentrated by evaporation under reduced pressure, and the residue is chromatographed over silica gel with toluene/ethyl acetate (7:1) and (6:1). The title compound is obtained in the form of a colourless, viscous oil. R$_f$ (toluene/ethyl acetate 1:1): 0.43; $[\alpha] = +88 \pm 1°$ (1.01% in chloroform). The $^1$H-NMR spectrum (400 MHz in CDCl$_3$) points to the existence of two rotamers in a ratio of 1.3:1.

(d)
(2R,3R)-N-p-methoxybenzyl-N-tert.-butylsulphonyl-methyl-2,3-epoxybutyramide

At −14° with the exclusion of moisture, 340 ml of 1,5-diazabicyclo[5.4.0]undec-5-ene in 1 ml of tetrahydrofuran are added to a solution of 486 mg (1.1 mmol) of (2S,3R)-N-p-methoxybenzyl-N-tert.-butylsulphonyl-methyl-2-bromo-3-hydroxybutyramide in 8 ml of tetrahydrofuran. The solution is stirred at room temperature for 75 minutes. After the addition of methylene chloride, the organic phase is extracted by shaking with 15% aqueous citric acid solution and 8% aqueous sodium bicarbonate solution. The organic phase is dried over sodium sulphate and concentrated by evaporation under reduced pressure. After chromatography of the residue over silica gel with toluene/ethyl acetate (4:1), the title compound is obtained in the form of a colourless, viscous oil. R$_f$ (toluene/ethyl acetate 1:1): 0.29; $[\alpha] = +45 \pm 1°$ (1.065% in CHCl$_3$). The $^1$H-NMR spectrum (400 MHz in CDCl$_3$) points to the existence of two rotamers in a ratio of 1:2.8.

(e)
(3S,4R)-1-p-methoxybenzyl-3-[(1′R)-1-hydroxyethyl]-4-tert.-butylsulphonyl-2-azetidinone To a solution of 398 mg (1.12 mmol) of (2R,3R)-N-p-methoxybenzyl-N-tert.-butylsulphonylmethyl-2,3-epoxybutyramide in 2.5 ml of tetrahydrofuran there are added dropwise, while stirring at 0° with the exclusion of moisture, 7 ml of a solution of dehydrated tetra-n-butylammonium fluoride in THF, prepared by dehydrating 5 g of tetra-n-butylammonium fluoride trihydrate at 55° and 0.1 torr and making up to 20 ml with tetrahydrofuran. Activated molecular sieve of 4Å is added to the reaction mixture and the whole is stirred for two hours. The molecular sieve is filtered off with suction and washed four times with 20 ml of methylene chloride each time. 5 parts of diethyl ether are added to each individual filtrate and the filtrates are washed in succession with aqueous phosphate buffer solution of pH 8. The combined organic phases are dried over magnesium sulphate and concentrated by evaporation under reduced pressure. The residue is chromatographed over 20 g of silica gel with toluene/ethyl acetate (3:1) and the crystalline title compound is obtained. M.p. 112°–113° (Kofler, from methylene chloride, diethyl ether, pentane); R$_f$ (toluene/ethyl acetate 1:1): 0.27; $[\alpha] = +9 \pm 1°$ (1.105% in chloroform); $^1$H-NMR spectrum (400 MHz in CDCl$_3$): $\delta = 4.65$ for proton (a) at the 4(R)-carbon atom, $\delta = 3.61$ for proton (b) at the 3(S)-carbon atom and $\delta = 4.09$ for proton (c) at the 1′(R)-carbon atom of the hydroxyethyl group; J a-b: approximately 2, J b-c: approximately 7.

(f)
(3S,4R)-1-p-methoxybenzyl-3-[(1′R)-1-allyloxycarbonyloxyethyl]-4-tert.-butylsulphonyl-2-azetidinone 0.68 g (2 mmol) of tetra-n-butylammonium bisulphate is added to a two-phase system consisting of a solution of 1.77 g (5 mmol) of (3S,4R)-1-p-methoxybenzyl-3-[(1′R)-1-hydroxyethyl]-4-tert.-butylsulphonyl-2-azetidinone in 20 ml of methylene chloride and 20 ml of a 1N aqueous sodium hydroxide solution. While stirring vigorously, there is added at 0° 0.8 ml (7.5 mmol) of chloroformic acid allyl ester. After 20 and 40 minutes, 0.8 ml of chloroformic acid allyl ester is again added thereto. After a reaction period of 60 minutes, methylene chloride is added to the mixture, the aqueous phase is separated off and the organic phase is washed in succession with 5% aqueous citric acid solution and with 8% aqueous sodium bicarbonate solution. After drying of the organic phase over sodium sulphate and concentration by evaporation under reduced pressure, a crude product is obtained as residue which is purified by chromatography over Merck silica gel with toluene/ethyl acetate (9:1). M.p. 90°–91°; R$_f$ (toluene/ethyl acetate 4:1): 0.43; $[\alpha] = +46° \pm 1°$ (1 49% in chloroform).

(g)
(3S,4R)-3-[(1′R)-1-allyloxycarbonyloxyethyl]-4-tert.-butylsulphonyl-2-azetidinone A solution of 2.46 g (4.48 mmol) of cerium(IV) ammonium nitrate in 6 ml of water is added at 0° to a solution of 518 mg (1.18 mmol) of (3S,4R)-1-p-methoxybenzyl-3-[(1′R)-1-allyloxycarbonyloxyethyl]-4-tert.-butylsulphonyl-2-azetidinone in 12 ml of acetonitrile, and the whole is stirred for one hour at room temperature. After extraction with ethyl acetate, drying of the organic phase over sodium sulphate and concentration by evaporation under reduced pressure, the crude product is obtained which is purified by chromatography over 20 g of Merck silica gel with toluene/ethyl acetate (4:1 and 1:1). M.p. 137°–138°; $[\alpha] = +49 \pm 1°$ (1.067% in chloroform); R$_f$ (toluene/ethyl acetate 1:1): 0.48.

(h)
(3S,4R)-3-[(1′R)-1-allyloxycarbonyloxyethyl]-4-triphenylmethylthioazetidin-2-one In a manner analogous to that described in Example 1(a), 0.86 g of (3S,4R)-3-[(1′R)-allyloxycarbonyloxyethyl]4-tert.-butylsulphonylazetidin-2-one is converted into the title compound.
IR (CH$_2$Cl$_2$) 3395, 1770, 1750 cm$^{-1}$.

(i)

2-[(3S,4R)-3-[(1'R)-1-allyloxycarbonyloxyethyl]-4-triphenylmethylthio-2-oxo-azetidin-1-yl]-2-hydroxyacetic acid allyl ester In a manner analogous to that described in Example 1(b), 0.82 g of (3S,4R)-3-[(1'R)-1-allyloxycarbonyloxyethyl]-4-tert.-butylsulphonylazetidin-2-one is converted into the title compound.

IR (CH$_2$Cl$_2$): 3510, 1770, 1745 cm$^{-1}$.

(k)

2-[(3S,4R)-3-[(1'R)-1-allyloxycarbonyloxyethyl]4-triphenylmethylthio-2-oxo-azetidin-1-yl]-2-triphenylphosphoranylideneacetic acid allyl ester In a manner analogous to that described in Example 1(c), 1 g of 2-[(3S,4R)-3-[(1'R)-allyloxycarbonyloxyethyl]-4-triphenylmethylthio-2-oxo-azetidin-1-yl]-2hydroxyacetic acid allyl ester is converted into the title compound.

IR (CH$_2$Cl$_2$): 1745, 1620 cm$^{-1}$.

(l) the silver salt of 2-[(3S,4R)-3-[(1'R)-1-allyloxycarbonyloxyethyl]-4-mercapto-2-oxo-azetidin-1-yl]-2-triphenylphosphoranylideneacetic acid allyl ester In a manner analogous to that described in Example 1(d), 0.46 g of 2-[(3S,4R)-3-[(1'R)-allyloxycarbonyloxyethyl]-4-triphenylmethylthio-2-oxo-azetidin-1-yl]-2triphenylphosphoranylideneacetic acid allyl ester is converted into the title compound.

IR (CH$_2$Cl$_2$): 1765, 1745, 1630 cm$^{-1}$.

(m)

2-[(3S,4R)-3-[(1'R)-1-allyloxycarbonyloxyethyl]-4-(allyloxycarbonylaminoacetylthio)-2-oxo-azetidin-1-yl]-2-triphenylphosphoranylideneacetic acid allyl ester In a manner analogous to that described in Example 1(e), 0.385 g of 2-[(3S,4R)-3-[(1'R)-1-allyloxycarbonyloxyethyl]-4-mercapto-2-oxo-azetidin-1-yl]-2-triphenylphosphoranylideneacetic acid allyl ester (silver salt) is converted into the title compound with allyloxycarbonylaminoacetyl chloride.

IR (CH$_2$Cl$_2$): 3440, 1750, 1740, 1700, 1620 cm$^{-1}$.

EXAMPLE 5

(5R,6S)-2-aminomethyl-6-[(1'R)-1-hydroxyethyl]-2-penem-3-carboxylic acid

To a solution of 425 mg of (5R,6S)-2-allyloxycarbonylaminomethyl-6-[(1'R)-1-allyloxycarbonyloxyethyl]-2-penem-3-carboxylic acid allyl ester in 20 ml of absolute THF there are added, at −10°, 60 mg of tetrakis-(triphenylphosphine)-palladium and then 1.07 ml of tributyltin hydride. After stirring for 20 minutes at −10°, 0.3 ml of acetic acid are added and, after removing the cooling bath, the reaction mixture is stirred for a further 30 minutes. After concentration in a rotary evaporator, the residue is taken up in water/ethyl acetate, the aqueous phase is separated off and the organic phase is extracted 3 times more with water. After brief concentration in a rotary evaporator, the combined aqueous phases are lyophilised. UV (phosphate buffer pH 7.4): $\lambda_{max.}$=308 nm; $\alpha_D^{20}$ (0.07% in water): +220°±11°.

EXAMPLE 6

(5R,6S)-2-(N-methyl-N-allyloxyoarbonylaminomethyl)-6-[(1'R)-1-allyloxycarbonyloxyethyl]-2-penem-3-carboxylic acid allyl ester In a manner analogous to that described in Example 4, 2.42 g of 2-[(3S,4R)-3-[(1'R)-1-allyloxycarbonyloxyethyl]-4-(N-methyl-N-allyloxycarbonylaminoacetyl-thio)-2-oxo-azetidin-1-yl]-2-triphenylphosphoranylideneacetic acid allyl ester are converted into the title compound.

IR (methylene chloride): 1780, 1745, 1705, 1580 cm$^{-1}$.

The starting material is manufactured as follows:

(a) N-allyloxycarbonylsarcosine

In a manner analogous to that described in Example 1(ea), 15 g of sarcosine are converted into the title compound.

IR (methylene chloride): 1705 cm$^{-1}$.

(b) N-allVloxycarbonylaminosarcosvl chloride

In a manner analogous to that described in Example 1(eb), 3.46 g of N-allyloxycarbonylsarcosine are converted into the title compound with 6.27 ml of thionyl chloride.

IR (methylene chloride): 1800, 1710 cm$^{-1}$.

(c)

2-[(3S,4R)-3-[(1'R)-1-allyloxycarbonyloxyethyl]-4-(N-methyl-N-allyloxycarbonylaminoacetylthio)-2-oxoazetidin-1-yl]-2-triphenylphosphoranylideneacetic acid allyl ester In a manner analogous to that described in Example 1(e), 3.75 g of the silver salt of 2-[(3S,4R)-3-[(1'R)-1-allyloxycarbonyloxyethyl]-4-mercapto-2-oxo-azetidin-1yl]-2-triphenylphosphoranylideneacetic acid allyl ester (cf. Example 4–1)) are converted into the title compound with 1.55 g of N-allyloxycarbonylsarcosyl chloride.

IR (methylene chloride): 1750, 1700, 1620 cm$^{-1}$.

EXAMPLE 7

2-(N-methylaminomethyl)-6-[(1'R)-1hydroxyethyl]-2-penem-3-carboxylic acid

In a manner analogous to that described in Example 5, 1.3 g of (5R,6S)-2-(N-methyl-N-allyloxycarbonylaminomethyl)-6-[(1'R)-1-allyloxycarbonyloxyethyl]-2-penem-3-carboxylic acid allyl ester are converted into the title compound.

UV (phosphate buffer pH 7.4) $\lambda_{max}$=311 nm.

EXAMPLE 8

(5R,6S)-2-(N-formamidinomethyl)-6-hydroxymethyl-2-penem-3-carboxylic acid

A solution of 23 mg of (5R,6S)-2-aminomethyl-6hydroxymethyl-2-penem-3-carboxylic acid and 8.4 mg of sodium bicarbonate in 1 ml of water is added at room temperature to a solution of 109.5 mg of ethyl formimidate hydrochloride and 84 mg of sodium bicarbonate in 4 ml of water. After stirring for 50 minutes at room temperature, 1 ml of 1N HCl is added and the whole is concentrated by evaporation under a high vacuum. The crude substance is purified by chromatography over OPTI-UPC$_{12}$.

UV (phosphate buffer pH 7.4): $\lambda_{max.}$=306.5 nm.

EXAMPLE 9

(5R,6S)-2-(N-formamidinomethyl)-6-[(1'R)-1-hydroxyethyl]-2-penem-3-carboxylic acid In a manner analogous to that described in Example 8, 51 mg of (5R,6S)-2-aminomethyl-6-[(1'R)-1-hydroxyethyl]-2-penem-3-carboxylic acid are converted into the title compound.

UV (phosphate buffer pH 7.4): $\lambda_{max}=310$ nm.

EXAMPLE 10

[(5R,6S)-2-chloromethyl-6-(tert.-butyldimethylsilyloxymethyl)-2-penem-3-carboxylic acid allyl ester In a manner analogous to that described in Example 1, 0.71 g of 2-[(3S,4R)-3-(tert.-butyldimethylsilyloxymethyl)-4-chloroacetylthio-2-oxo-azetidin-1-yl]-2-triphenylphosphoranylideneacetic acid allyl ester is converted into the title compound.

IR (methylene chloride): 1790, 1705, 1560 cm$^{-1}$.

The starting material is manufactured as follows:

2-(3S,4R)-3-(tert.-butyldimethylsilyloxymethyl)-4-chloroacetylthio-2-oxo-azetidin-1-yl]-2-triphenylphosphoranylideneacetic acid allyl ester 30 g of the silver salt of 2-[(3S,4R)-3-(tert.-butyldimethylsilyloxymethyl)-4-mercapto-2-oxo-azetidin-1-yl]-2-triphenylphosphoranylideneacetic acid 2-allyl ester (Example 1d)) are dissolved in 600 ml of absolute methylene chloride, the solution is cooled to 0° and 120 mg of 4-dimethylaminopyridine and 6.8 ml of pyridine are added thereto. After the addition of 5.04 ml of chloroacetyl chloride and an additional 1.5 ml of pyridine, the reaction mixture is stirred at 0° for 30 minutes. The precipitate is filtered off and the filtrate is washed with aqueous NaHCO$_3$ solution and then with brine, is dried over Na$_2$SO$_4$ and concentrated by evaporation. After purification over silica gel (eluant toluene/ethyl acetate 9:1), the pure title compound is obtained. TLC (silica gel, toluene/ethyl acetate 1:1): R$_f$=0.5; IR (CH$_2$Cl$_2$): 1750, 1680, 1610 cm$^{-1}$.

EXAMPLE 11

(5R,6S)-2-azidomethyl-6-(tert.-butyl-dimethylsilyloxymethyl)-2-penem-3-carboxylic acid allyl ester 4.04 g of (5R,6S)-2-chloromethyl-6-(tert.-butyldimethylsilyloxymethyl)-2-penem-3-carboxylic acid allyl ester are dissolved in 40 ml of DMF and 0.9 g of sodium azide is added thereto. After stirring for 6 hours, the solvent is reduced to a fifth of the volume and the residue is partitioned between ethyl acetate and water. After drying over sodium sulphate, the solvent is evaporated off. The crude mixture is purified by chromatography over silica gel (eluant toluene/ethyl acetate): IR (methylene chloride): 2110, 1790, 1705, 1585 cm$^{-1}$.

EXAMPLE 12

(5R,6S)-2-azidomethyl-6-hydroxymethyl-2-penem-3-carboxylic acid allyl ester

In a manner analogous to that described in Example 2, 1.2 g of (5R,6S)-2-azidomethyl-6-(tert.-butyldimethylsilyloxymethyl)-2-penem-3-carboxylic acid allyl ester is converted into the title compound.

IR (methylene chloride): 3595, 2120, 1790, 1710, 1585 cm$^{-1}$.

EXAMPLE 13

(5R,6S)-2-azidomethyl-6-hydroxymethyl-2-penem-3-carboxylic acid

In a manner analogous to that described in Example 3, 0.89 g of (5R,6S)-2-azidomethyl-6-hydroxymethyl-2-penem-3-carboxylic acid allyl ester is converted into the title compound.

UV (phosphate buffer pH 7.4): $\lambda_{max.}=309$ nm.

EXAMPLE 14

(5R,6S)-2-aminomethyl-6-hydroxymethyl-2-penem-3-carboxylic acid 0.53 g of (5R,6S)-2-azidomethyl-6-hydroxymethyl-2-penem-3-carboxylic acid is dissolved in 10 ml of a mixture of THF/water (1:1) and hydrogenated in the presence of 0.53 g of 10% palladium-on-carbon for 4 hours at room temperature under normal pressure. Filtration and concentration are then carried out and the crude mixture is purified by reverse-phase column chromatography (eluant: water).

UV (phosphate buffer pH 7.4): $\lambda_{max.}=309$ nm.

The product is identical with the compound manufactured according to Example 3.

EXAMPLE 15

(5R,6S)-2-(allyloxycarbonylaminomethyl)-6-[(1'R)-1-allyloxycarbonyloxyethyl]-2-penem-3-carboxylic acid allyl ester 317 mg (0.852 mmol) of (3S,4R)-3-(1-allyloxy- carbonyloxyethyl)-4-allyloxycarbonylaminoacetylthioazetidin-2-one are dissolved in 5 ml of methylene chloride and the solution is cooled to 15° 0.143 ml (1.28 mmol) of allyloxyoxalyl chloride and 0.217 ml of Hunig base are then added thereto and the whole is stirred at −15° for 30 minutes. The reaction solution is washed once with 0.1N HCl (cooled) and twice with saturated sodium chloride solution, dried over sodium sulphate and concentrated in a rotary evaporator. The residue is extracted twice with toluene in a rotary evaporator.

The oily residue, containing crude 2-[(3S,4R)-3-[(1'R)-1-allyloxycarbonyloxyethylaminoacetylthio-2-oxo-azetidin-1-yl]-4-allyloxycarbonyl]-2-oxo-acetic acid allyl ester, is dissolved in 20 ml of toluene, and 0.32 ml of triethyl phosphite is added thereto and the whole is heated at 103° under argon for 17 hours. The solution is concentrated and purified over silica gel by preparative thin-layer chromatography (system: toluene/ethyl acetate 3:1). The product is identical with that described in Example 4.

The starting material, (3S,4R)-3-(1-allyloxycarbonyloxyethyl)-4-allyloxycarbonylaminoacetylthioazetidin-2-one, is manufactured as follows:

450 mg (2.57 mmol) of allyloxycarbonylaminothioacetic acid are made into a slurry in 4 ml of water and, at room temperature under a nitrogen atmosphere, 2.5 ml of 1N sodium hydroxide solution are added thereto; there is then added a solution of 585 mg (1.83 mmol) of (3S,4R)-3-[(1'R)-1-allyloxycarbonyloxymmol) ethyl]-4-tert.-butylsulphonylazetidin-2-one (cf. Example 4g)) in 5 ml of methylene chloride and the emulsion is stirred vigorously for 1 hour at room temperature under a nitrogen atmosphere. The reaction mixture is partitioned and the organic phase is washed twice with saturated sodium chloride solution. The aqueous phases are extracted twice with methylene chloride. The organic solutions are dried over sodium sulphate and concentrated in a rotary evaporator. The crude product is purified by preparative thin-layer chromatography (system: hexane/ether 1:9).

EXAMPLE 16

In a manner analogous to that described in the preceding Examples, the following compounds can be manufactured using the corresponding starting compounds:

(5R,6S)-2-(N-acetamidinomethyl)-6-hydroxymethyl-2-penem-3-carboxylic acid

UV (phosphate buffer pH 7.4) $\lambda_{max}=307$ nm.

(5R,6S)-2-(N-acetamidinomethyl)-6-[(1'R)-1-hydroxyethyl]-2-penem-3-carboxylic acid UV (phosphate buffer pH 7.4) $\lambda_{max}=311$ nm.

(5R,6S)-2-(N-guanidinylmethyl)-6-hydroxymethyl-2-penem-3-carboxylic acid

UV {phosphate buffer pH 7.4) $\lambda_{max.}=306$ nm.

(5R,6S)-2-(N-guanidinylmethyl)-6-[(1'R)-1-hydroxyethyl]-2-penem-3-carboxylic acid UV (phosphate buffer pH 7.4) $\lambda_{max.}=310$ nm.

(5R,6S)-2-(N-ethylaminomethyl)-6-[(1'R)-1-hydroxyethyl]-2-penem-3-carboxylic acid UV (phosphate buffer pH 7.4) $\lambda_{max.}=310$ nm.

(5R,6S)-2-(N-ethylaminomethyl)-6-hydroxymethyl-2-penem-3-carboxylic acid

UV (phosphate buffer pH 7.4) $\lambda_{max}=311$ nm.

(5R,6S)-2-(N-propylaminomethyl)-6-[(1'R)-1-hydroxyethyl]-2-penem-3-carboxylic acid UV (phosphate buffer pH 7.4) $\lambda_{max}=312$ nm.

(5R,6S)-2-(N-propylaminomethyl)-6-hydroxymethyl-2-penem-3-carboxylic acid

UV (phosphate buffer pH 7.4) $\lambda_{max}=311$ nm.

(5R,6S)-2-(N-methylaminomethyl)-6-hydroxymethyl-2-penem-3-carboxylic acid

UV (phosphate buffer pH 7.4) $\lambda_{max.}=306$ nm.

EXAMPLE 17

(5R,6S)-2-aminomethyl-6-hydroxymethyl-2-penem-3-carboxylic acid 1-ethoxycarbonyloxyethyl ester 1.2 g of sodium iodide are dissolved in 3.7 ml of acetone, and 0.275 ml of ethyl-1-chloroethyl carbonate is added thereto. The mixture is stirred at room temperature for 3 hours. The solution is then added dropwise to 15.0 ml of methylene chloride and the inorganic salts which precipitate are filtered off. The methylene chloride solution is concentrated to a volume of 2 ml and added, at 0°, to a solution of 0.23 g (1 mmol) of (5R,6S)-2-aminomethyl-6-hydroxy- methyl-2-penem-3-carboxylic acid in 4 ml of dimethylacetamide. The mixture is then stirred for 3 hours at 0°, then diluted with ethyl acetate and washed three times with water. The organic phases are dried over sodium sulphate and concentrated in a rotary evaporator. The crude product is purified over 10 g of silica gel with the eluant ethyl acetate. The title compound is obtained in the form of a white foam.

IR spectrum (methylene chloride): absorption bands at 1790 and 1740 cm$^{-1}$.

EXAMPLE 18

(5R,6S)-2-aminomethyl-6-hydroxymethyl-2-penem-3-carboxylic acid pivaloyloxymethyl ester 0.6 g of sodium iodide is dissolved in 2 ml of acetone, and 0.15 ml of pivalic acid chloromethyl ester is added thereto. The mixture is stirred at room temperature for 3 hours and then added dropwise to 7.5 ml of methylene chloride. The inorganic salts which precipitate are filtered off. The methylene chloride solution is concentrated to a volume of 1 ml and added, at 0°, to a solution of 0.092 g (0.4 mmol) of (5R,6S)-2-aminomethyl-6-hydroxymethyl-2-penem-3-carboxylic acid and 0.07 ml of diisopropylethylamine in 4 ml of N,N-dimethylacetamide. The mixture is then stirred at 0° for 3 hours and is subsequently diluted with ethyl acetate and washed three times with water. The organic phase is dried over sodium sulphate and concentrated in a rotary evaporator. The crude product is purified over 10 g of silica gel with the eluant ethyl acetate. The title compound is obtained in the form of a white foam. IR spectrum (methylene chloride): absorption bands at 1790 and 1730 cm$^{-1}$.

EXAMPLE 19

In a manner analogous to that described in the preceding Examples, the following compounds are obtained:

(5R, 6S)-2-aminomethyl-6-[(1'R)-1-hydroxyethyl]-2-penem(3-carboxylic acid 1-ethoxycarbonyloxyethyl ester IR (CH$_2$Cl$_2$) 1785, 1740 cm$^{-1}$.

(5R,6S)-2-aminomethyl-6-[(1'R)-1-hydroxyethyl]-2-penem-3-carboxylic acid pivaloyloxymethyl ester IR (CH$_2$Cl$_2$) 1790, 1735 cm$^{-1}$.

EXAMPLE 20

Dry ampoules or phials, each containing 0.5 g of (5R,6S)-2-aminomethyl-6-[(1'R)-1-hydroxyethyl]-2-penem-3-carboxylic acid as active ingredient, are prepared as follows:

| Composition (for 1 ampoule or phial): | |
| --- | --- |
| active ingredient | 0.5 g |
| mannitol | 0.05 g |

A sterile aqueous solution of the active ingredient and the mannitol is subjected to freeze-drying under aseptic conditions in 5 ml ampoules or 5 ml phials, and the ampoules or phials are sealed and checked.

Instead of the above-mentioned active ingredient, it is also possible to use the same amount of another active ingredient of the preceding Examples, such as, for example, (5R,6S)-2-aminomethyl-6-hydroxymethyl-2-penem-3-carboxylic acid.

I claim:

1. (5R,6S)-2-aminomethyl-6-hydroxymethyl-2-penem-3-carboxylic acid and pharmaceutically acceptable salts thereof in substantially pure form 2. 2-(N-methylaminomethyl)-6-[(1'R)-1-hydroxyethyl]-2-penem-3-carboxylic acid and pharmaceutically acceptable salts thereof in substantially pure form.

3. (5R,6S)-2-aminomethyl-6-[(1'R)-1-hydroxyethyl]-2-penem-3-carboxylic acid and pharmacuetuically acceptable salts thereof in substantially pure form.

4. A pharmaceutical preparation comprising an antibacterially effective amount of a substantially pure compound selected from (5R,6S)-2-aminomethyl-t-hydroxymethyl-2-penem-3-carboxylic acid; (5R,6S)-2-(N-methylaminomethyl)-6-[(1'R)-1'-hydroxyethyl]-2-penem-3-carboxylic acid; and (5R,6S)-2-aminomethyl-6-[(1'R)1'-hydroxyethyl]-2penem-3carboxylic acid or pharmaceutically acceptable salts thereof and a pharmaceutically acceptabel carrier.

5. A method of treating a bacterial infection in a mammal in need of such treatment comprising administering to said mammal an antibacterially effective amount of a substantially pure compound selected from (5R,6S)-2-aminomethyl-6-hydroxymethyl-2-penem-3-carboxylic acid; (5R,6S)-2-(N-methylaminomethyl)-6-[(1'R)-1'-hydroxyethyl]-2-penem-3-carboxylic acid; and (5R,6S)-2-aminomethyl-6-[(1'R)-1'-hydroxyethyl]-2-penem-3-carboxylic acid or a pharmaceutically acceptable salt thereof.

* * * * *